(12) United States Patent
Chae et al.

(10) Patent No.: US 11,382,880 B2
(45) Date of Patent: Jul. 12, 2022

(54) METHOD FOR IMPROVING DIGESTIVE HEALTH

(71) Applicants: Brightseed, Inc., San Francisco, CA (US); Sanford-Burnham Medical Research Institute, La Jolla, CA (US)

(72) Inventors: Lee Heil Chae, San Francisco, CA (US); Fred Levine, La Jolla, CA (US)

(73) Assignees: Brightseed, Inc., South San Francisco, CA (US); Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 17/140,979

(22) Filed: Jan. 4, 2021

(65) Prior Publication Data

US 2021/0128499 A1    May 6, 2021

Related U.S. Application Data

(63) Continuation of application No. PCT/US2020/043753, filed on Jul. 27, 2020.

(60) Provisional application No. 62/879,727, filed on Jul. 29, 2019.

(51) Int. Cl.

| | | |
|---|---|---|
| *A61K 36/00* | (2006.01) | |
| *A61K 31/165* | (2006.01) | |
| *A23L 33/105* | (2016.01) | |
| *A23L 33/00* | (2016.01) | |
| *A61P 1/14* | (2006.01) | |
| *A61K 36/185* | (2006.01) | |
| *A61K 36/21* | (2006.01) | |
| *A61K 36/31* | (2006.01) | |
| *A61K 36/39* | (2006.01) | |
| *A61K 36/47* | (2006.01) | |
| *A61K 36/67* | (2006.01) | |
| *A61K 36/69* | (2006.01) | |
| *A61K 36/725* | (2006.01) | |
| *A61K 36/758* | (2006.01) | |
| *A61K 36/81* | (2006.01) | |
| *A61K 36/815* | (2006.01) | |
| *A61K 36/8962* | (2006.01) | |
| *A61K 36/899* | (2006.01) | |

(52) U.S. Cl.
CPC .......... *A61K 31/165* (2013.01); *A23L 33/105* (2016.08); *A23L 33/40* (2016.08); *A61K 36/185* (2013.01); *A61K 36/21* (2013.01); *A61K 36/31* (2013.01); *A61K 36/39* (2013.01); *A61K 36/47* (2013.01); *A61K 36/67* (2013.01); *A61K 36/69* (2013.01); *A61K 36/725* (2013.01); *A61K 36/758* (2013.01); *A61K 36/81* (2013.01); *A61K 36/815* (2013.01); *A61K 36/899* (2013.01); *A61K 36/8962* (2013.01); *A61P 1/14* (2018.01); *A23V 2002/00* (2013.01); *A61K 2236/333* (2013.01)

(58) Field of Classification Search
CPC ...................................................... A61K 36/00
USPC ........................................................ 424/725
See application file for complete search history.

(56) References Cited

U.S. PATENT DOCUMENTS

| | | | |
|---|---|---|---|
| 5,605,793 A | 2/1997 | Stemmer | |
| 5,811,238 A | 9/1998 | Stemmer et al. | |
| 5,830,721 A | 11/1998 | Stemmer et al. | |
| 5,837,458 A | 11/1998 | Minshull et al. | |
| 6,265,185 B1 | 7/2001 | Muller et al. | |
| 6,316,209 B1 | 11/2001 | Baekkeskov et al. | |
| 6,368,837 B1 | 4/2002 | Gatenby et al. | |
| 6,391,651 B1 | 5/2002 | Maclaren et al. | |
| 6,521,748 B2 | 2/2003 | Tang | |
| 7,666,455 B2 | 2/2010 | Resurreccion et al. | |
| 8,481,593 B2 | 7/2013 | Okombi | |
| 9,089,499 B2 | 7/2015 | Okombi | |
| 9,227,898 B2 | 1/2016 | Boue et al. | |
| 11,173,136 B2 | 11/2021 | Chae | |
| 2003/0152682 A1 | 8/2003 | Ley | |
| 2004/0198656 A1 | 10/2004 | Najib et al. | |
| 2004/0234657 A1 | 11/2004 | Rowley et al. | |
| 2007/0183996 A1* | 8/2007 | Okombi .................. | A61K 8/42 424/62 |
| 2008/0132544 A1 | 6/2008 | Kitano | |
| 2009/0324761 A1 | 12/2009 | Khoo et al. | |
| 2022/0062207 A1 | 3/2022 | Chae | |

FOREIGN PATENT DOCUMENTS

| | | |
|---|---|---|
| EP | 1 671 534 | 6/2006 |
| GB | 2431876 | 5/2007 |
| JP | 2012-149004 | 8/2012 |
| JP | 5207341 B2 | 6/2013 |
| KR | 2005/0091116 | 9/2005 |

(Continued)

OTHER PUBLICATIONS

Ahn et al., Hepatocyte Nuclear Factor 4α in the Intestinal Epithelial Ceils Protects Against Inflammatory Bowel Disease, Inflammatory Bowel Diseases, 14(7, pp. 908-920, (2008).

Al-Taweel et al., 2012, Bioactive Phenolic Amides from Celtis Africana, Molecules, 17:2675-2682.

Amaro et al., 2014, Hypoglycemic and hypotensive activity of a root extract of Smilax aristolochiifolia, standardized on N-trans-feruloyl-lyramine, Molecules, 19:11366-11384.

Amin et al., 2006, The Protective Effect of Tribulus terrestris in Diabetes, Ann. NY Acad. Sci 1084:391-401.

(Continued)

*Primary Examiner* — Michael V Meller
(74) *Attorney, Agent, or Firm* — Knobbe, Martens, Olson & Bear, LLP

(57) ABSTRACT

Disclosed herein are methods for improving digestive health by providing a consumable composition. Some embodiments provided include, for example, administering a compound of Formula (I) or compound of Formula (II). Some embodiments provide the composition is formulated as a dietary supplement, food ingredient or additive, a medical food, nutraceutical or pharmaceutical composition.

20 Claims, 5 Drawing Sheets

(56) References Cited

FOREIGN PATENT DOCUMENTS

| KR | 2013-0104240 | | 9/2013 |
|---|---|---|---|
| KR | 1020160015174 | * | 2/2016 |
| WO | WO 04/101757 | | 11/2004 |
| WO | WO 2008/154083 A3 | | 12/2008 |
| WO | WO2017168422 | * | 10/2017 |
| WO | WO 18/161077 | | 9/2018 |
| WO | WO 2019073127 | * | 4/2019 |

OTHER PUBLICATIONS

Appert et al., 1994, Structural and catalytic properties for the four phenylalanine ammonia-lyase isoenzymes from parsley (*Petroselinum crispum* Nym.), Eur. J. Biochem. 225:491-499.

Ausubel et al., 1987, In Current Protocols in Molecular Biology, Wiley-Interscience (TOC).

Babeu et al., 2014, Hepatocyte Nuclear Factor 4-Alpha Involvement in Liver and Intestinal Inflammatory Networks, World Journal of Gastroenterology, 20(1):22-30.

Baez-Viveros et al., 2004, Metabolic engineering and protein directed evoution increase the yield of L-phenylalanine synthesized from glucose in *Escherichia coli*, Biotechnol. Bioeng. 87:516-524.

Bandoni et al., 1968, Phenylalanine and tyrosine ammonia-lyase activity in some basidiomycetes, Phytochemistry 7: 205-207.

Becker et al., 1991, High-efficiency transformation of yeast by electroporation, in Guthrie ed., Methods in Enzymology, 194:186-187.

Berry, 1996, Improving production of aromatic compounds in *Escherichia coli* by metabolic engineering, Trends Biotechnol. 14:250-256.

Bradford, 1976, A rapid and sensitive method for the quantitation of microgram quantities of protein utilizing the principle of protein-dye binding, Anal. Biochem. 72:248-254.

Braus, Sep. 1991, Aromatic amino acid biosynthesis in the yeast *Saccharaomyces cerevisiae*: a model system for the regulation of a eukaryotic biosynthetic pathway, Microbiol Rev. 55:349-370.

Bruning et al., 2000, Role of Brain Insulin Receptor in Control of Body Weight and Reproduction, Science, 289:.2122-2125.

Brunt et al., 1999, Nonalcoholic Steatohepatitis: A Proposal for Grading and Staging the Histological Lesions, The American Journal of Gastroenterology, 94(9):2467-2474.

Butler et al., 2000, A Unique Metabolic Syndrome Causes Obesity in the Melanocortin-3 Receptor-Deficient Mouse, Endocrinology, 141(9):3518-3521.

Cai et al., 2006, Peptide deformyiase is a potential target for anti-Heiicobacter pylori drugs: Reverse docking, enzymatic assay, and X-ray crystallography validation, Protein Science, 15:2071-2081.

Cantos et al., 2000, Effect of postharvest ultraviolet irradiation on resveratrol and other phenolics on Cv. Napoleon table grapes, J. Agric. Food Chem. 48:4606-4612.

Carmiel-Haggai et al., 2005, A High-Fat Diet Leads to the Progression of Non-Alcoholic Fatty Liver Disease in Obese Rats, The FASEB Journal, 19(1):136-138.

Cattin et al., 2009, Hepatocyte Nuclear Factor 4α, a Key Factor for Homeostasis, Cell Architecture, and Barrier Function of the Adult Intestinal Epithelium, Molecular and Cellular Biology, 29(23):6294-6308.

Chahar et al., 2014, Chromatin Profiling Reveals Regulatory Network Shifts and a Protective Role for Hepatocyte Nuclear Factor 4α during Colitis, Molecular and Cellular Biology, 34(17):3291-3304.

Chatzigeorgiou et al. 2009, The Use of Animal Models in the Study of Diabetes Meilitus, In Vivo, 23:245-258.

Chen et al., 2000, Inactivation of the Mouse Melanocortin-3 Receptor Results in Increased Fat Mass and Reduced Lean Body Mass, Nature Genetics, 26(1):97-102.

Chen et al., Mar. 4, 2012, The isolation and identification of two compounds with predominant radical scavenging activity in hempseed, Food Chemistry, 134(2):1039-1037.

Chiba et al., 2006, The Nuclear Receptor Hepatocyte Nuclear Factor 4α Acts as a Morphogen to Induce the Formation of Microvilli, Journal of Cell Biology, 175(6):971-980.

Cho et al., Jan. 1, 2011, Study on the hypochlolesterolemic and antioxidative effects of tyramine derivatives from the root bark of Lycium chenes Miller, Nutrition Research and Practice, 5(5).

Choi et al., 2009, Increased production of S-adenysol-L-methionine using recombinant *Saccharomyces cerevisiae* sake K6, Korean J. Chem. Eng. 26(1):156-159.

Clegg et al., 2011, Consumption of a High-Fat Diet Induces Central Insulin Resistance Independent of Adiposity, Physiology & Behavior, 103(1):10-16.

Darsigny et al., 2009, Loss of Hepatocyte-Nuclear-Factor-4α Affects Colonic Ion Transport and Causes Chronic Inflammation Resembling Inflammatory Bowel Disease in Mice, PLoS One, 4(10):e7609.

Davison et al., 2017, Microbiota Regulate Intestinal Epithelial Gene Expression by Suppressing the Transcription Factor Hepatocyte Nuclear Factor 4 Alpha, Genome Research, 27:1195-1206.

Deaner et al., 2017, Systematic testing of enzyme perturbation sensitivities via graded dCas9 modulation in *Saccaromyces cerevisiae*, Metab. Eng. 40:14-22.

Deshpande, 1992, Ethanol production from cellulose by coupled saccharification/fermentaion using *Saccharomyces cerevisiae* and cellulase complex from Scherotium rolfsii UV-8 mutant, Appl. Biochem. Biotechnol., 36:227-234.

Douglas, 1996, Phenylpropanoid metabolism and lignin biosynthesis: from weeds to trees. Trends Plant Sci 1:171-178.

Drel et al., 2006, The Leptin-Deficient (ob/ob, Mouse: A New Animal Model of Peripheral Neuropathy of Type 2 Diabetes and Obesity, Diabetes, 55(12):3335-3343.

Ehlting et al., 1999, Three 4-coumarate:coenzyme A ligases in *Arabidopsis thaliana* represent two evolutionarily divergent classes in angiosperms, The Plant Journal 19(1):9-20.

Eichholz et al., 2011, UV-B-induced changes of volatile metabolites and phenolic compounds in blueberries (*Vaccimium corymbosum* L.), Food Chem. 126:60-64.

Emes et al., 1970, Partial purification and properties of L-phenylalanine ammonia-lyase from streptomyces verticillatus. Can. J. Biochem. 48:613-622.

Engels et al., 2018, Inhibition of Pro-Inflammatory Functions of Human Neutrophils by Constituents of Melodorum fruticosum Leaves, Chemistry & Biodiversity, 15:1-14.

Figlewicz et al., 1986, Brain Insulin Binding is Decreased in Wistar Kyoto Rats Carrying the 'fa' Gene, Peptides, 7(1):61-65.

Galanie et al., Sep. 4, 2015, Complete biosynthesis of opioids in yeast, Science, 349(6252):1095-1100.

Geisel et al., 2003, The Impact of Hyperhomocysteinemia as a Cardiovascular Risk Factor in the Prediction of Coronary Heart Disease, Clinical Chemistry and Laboratory Medicine, 41(11):1513-1517.

Gupta et al., 2005, The MODY1 Gene HNF-4alpha Regulates Selected Genes Involved in Insulin Secretion, Journal of Clinical Investigation, 115(4):1006-1015.

Hagel et al., 2005, Elevated tyrosine decarboxylase and tyramine hydroxycinnamoyltransferase levels increase wound-induced tyramine-derived hydroxycinnamioc acid amide accumulation in transgenic tobacco leaves, Planta, 221:904-914.

Hanson et al., 1981, Phenylalanine ammonia-Lyase, Biochem. Plants, 7:577-625.

Hanson et al., 1972, The enzymic elimination of ammonica, in The Enzymes (3rd ed., Boyer Ed., Academic: New York) pp. 75-167.

Hariri et al., 2010, High-Fat Diet-Induced Obesity in Animal Models, Nutrition Research Reviews. 23(2):270-299.

Havir et al., 1971, L-phenylalanine ammonia-lyase (Maize), Plant Physiol. 48:130-136.

Hayhurst et al., 2001, Hepatocyte Nuclear Factor 4α (Nuclear Receptor 2A1, Is Essential for Maintenance of Hepatic Gene Expression and Lipid Homeostasis, Molecular and Cellular Biology, 21(4):1393-1403.

Hodgins, May 10, 1971, Yeast phenylalanine ammonia-lyase, J. Biol. Chem. 246(9):2977-2985.

(56) References Cited

OTHER PUBLICATIONS

Hohlfeld et al., 1995, Partial purification and characterization of hydroxycinnamoyl-coenzyme a:tyramine hydroxycinnamoyltransferase from cell suspension cultures of solanum tuberosum, Plant Physiol. 107:545-552.
Hummel at al., 1972, The Influence of Genetic Background on Expression of Mutations at the Diabetes Locus in the Mouse. I. C57BL-KsJ and C57BL-6J Strains, Biochemical Genetics, 7(1):1-13.
Huszar et al., 1997, Targeted Disruption of the Melanocortin-4 Receptor Results in Obesity in Mice, Cell, 88(1):131-141.
Huyskens-Keil et al., 2007, UV-B induced changes of phenol composition and antioxidant activity in black curant fruit (*Ribes nigrum* L.), J. Appl. Bot. Food Qual. 81:140-144.
Ikeda et al., 2006, Towards bacterial strains overproducing L-tryptophan and other aromatics by metabolic engineering, Appl. Microbial. Biotechnol. 69:615-626.
Inoue et al., 2002, Defective Ureagenesis in Mice Carrying a Liver-specific Disruption of Hepatocyte Nuclear Factor 4α (HNF4α, HNF4α Regulates Ornithine Transcarbamylase In Vivo*, The Journal of Biological Chemistry, 277:25257-252625.
Jiang et al., 2003, Expression and Localization of P1 Promoter-Driven Hepatocyte Nuclear Factor-4α (HNF4α, isoforms in Human and Rats, Nuclear Receptor, 1:1-12.
Joost. 2010, The Genetic Basis of Obesity and Type 2 Diabetes: Lessons from the New Zealand Obese Mouse, a Polygenic Model of the Metabolic Syndrome, Results and Problems in Cell Differentiation, 52:1-11.
Kang et a., 2009, Production of plant-specific tyramine derivatives by dual expression of tyramine N-hydroxycinnamoyltransferase and 4-coumarate:coenzyme A ligase in *Escherichia coli*, Biotechnol Lett, 31:1469-1475.
Keller et al., 1996, Changes in the accumulation of soluble and cell wall-bound phenolics in elicitor-treated cell suspension cultures and fungus-infected leaves of solanum tuberosum, Phytochemistry 42:389-396.
Kennedy et al., 2010, Mouse Models of the Metabolic Syndrome, Disease Models & Mechanisms, 3(3-4):156-166.
Kikuchi et al., Feb. 1997, Mutational analysis of the feedback sites of phenylalanine-sensitive 3-Deoxy-d-arabino-heptulosonate-7-phosphate synthase of *Escherichia coli*, Appl. Environ. Microbiol. 63(2):761-762.
King et al., 2005, Characterization of Cross-Linked Hydroxycinnamic Acid Amides Isolated from Potato Common Scab Lesions, Phytochemistry, 66(20):2468-2473.
King, 2012. The Use of Animal Models in Diabetes Research, British Journal of Pharmacology, 166(3):877-894.
Kiselyuk et al., 2010, Phenothiazine neuroleptics signal to the human insulin promoter as evealed by a novel high-throughput screen, J Biomol. Screen 15(6):663-670.
Kiselyuk et al., 2012, HNF4α Antagonists Discovered by a High-Throughput Screen for Modulators of the Human Insulin Promoter, Chem Biol 19(7):806-818.
Kitahata et al., 1989, Production of Rubusoside Derivatives by Transgalactosylation of Various β-Galactosidases, Agricultural and Biological Chemistry, 53:.2923-2928.
Kleiner et al., 2005, Design and Validation of a Histological Scoring System for Nonalcoholic Fatty Liver Disease, Hepatology, 41(6):1313-1321.
Knobloch et al., 1977, 4-Coumarate:CoA ligase from ceil suspension cultures of Petroselinum hortense Hoffm., Arch. Biochem. Biophys. 184:237-248.
Ko et al. 2015, N-trans-p-caffeoyl tyramine isolated from Tribulus terrestris exerts anti-inflammatory effects in lipopolysaccharide-stimulated RAW 264.7 cells International Journal of Molecular Medicine, 36:1042-1048.
Koopman et al., 2012, Do novo production of the flavonoid naringenin in engineered *Saccharomyces cerevisiae*, Microb. Cell Fact. 11:155.
Koukol et al., Oct. 1961, The metabolism of aromatic compounds in higher plants, J. Biol. Chem. 236(10):2692-2698.

Lee et al., 1996, Two divergent members of a tobacco 4-coumarate:coenzyme A Ligase (4CL, gene family, Plant Physiol. 112:193-205.
Lee et al., 2013, Reversal of Lipotoxic Effects on the Insulin Promoter by Aiverine and Benfluorex: Identification as HNF4a Activators, ACS Chem Biol 8(8):1730-1736.
Lee et al., 2017, Anti-inflammatory effect of tribulusamide D isolated from Tribulus terrestris in lipopolysaccharide-stirnulated RAW264.7 macrophages, Molecular Medicine Report, 16:4421-4428.
Lee et al., 2021, Liver fat storage is controlled by HNF4α through induction of lipophagy and is reversed by a potent HNF4α agonist Cell Death & Disease, 2021, 18 pages.
Leiter et al., 2004, Differential Levels of Diabetogenic Stress in Two New Mouse Models of Obesity and Type 2 Diabetes, Diabetes, 53(Suppl 1):S4-S11.
Leiter, 2009, Chapter 1: Selecting the Right Mouse Model for Metabolic Syndrome in Type 2 Diabetes Research: Methods in Molecular Biology, 560:1-17.
Leung et al., Aug. 1989, A method for random mutagenesis of a defined DNA segment using a modified polymerase chain reaction, Technique, 1(1):11-15.
Levin et al., 1997, Selective Breeding for Diet-Induced Obesity and Resistance in Sprague-Dawley Rats, American Journal of Physiology, 273:R725-730.
Lobov et al., 1991, Enzymic Production of Sweet Stevioside Derivatives: Transglucosylation by glucosidases, Agricultural and Biological Chemistry, 55(12):2959-2965.
Lovdal et al., 2010, Synergetic effects of nitrogen depletion, temperature, and light on the content of phenolic compounds and gene expression in leaves of tomato, Phytochemistry 71:605-613.
Ludidi et al., May 15, 2015, The Intestinal Barrier in Irritable Bowel Syndrome: Subtype-Specific Effects of the Systemic Compartment in an in Vitro Model, PLoS One, 10(5):e0123498.
Ludwig et al., 1980, Nonalcoholic Steatohepatitis: Mayo Clinic Experiences With a Hitherto Unnamed Disease, Mayo Clinic Proceedings, 55(7):434-438.
Lutke-Eversloh et al., 2008, Combinatorial pathway analysis for improved L-tyrosine production in *Escherichia coli*: identification of enzymative bottlenecks by systematic gene overexpression, Metabolic Engineering 10:68-77.
Luttik et al., 2008, Alleviation of feedback inhibition in *Saccharomyces cerevisiae* aromatic amino acid biosynthesis: quantification of metabolic impact, Metab. Eng. 10:141-153.
Maciel et al., 2016, New Alcamide and Anti-oxidant Activity of Pilosocereus gounellei A. Weber ex K. Schum. Bly. Ex Rowl. (Cactaceae), Molecules, 21:1-13.
Mao et al., 2017, Combinatorial analysis of enzymatic bottlenecks of L-tyrosine pathway by p-coumaric acid production in *Saccharamyces cerevisiae*, Biotechnol. Lett. 39(7):977-982.
Martinez-Jimenez et al., 2010, Hepatocyte Nuclear Factor 4α Coordinates a Transcription Factor Network Regulating Hepatic Fatty Acid Metabolism, Molecular and Cellular Biology, 30(3):565-577.
Matsuoka et al., 2015, Preserving Mafa Expression in Diabetic Islet β-cells Improves Glycemic Control in Vivo, Journal of Biological Chemistry, 290(12):7647-7657.
Millar et al., 2005, Determining hepatic Triglyceride Production in Mice:Comparison of Poloxamer 407 with Triton WR-1339, Journal of Lipid Research, 46:2023-2028.
Miller et al., 1987, Production of phenylalanine and organic acids by phosphoenol pyruvate carboxylase-dificient mutants of *Escherichia coli*, J. Ind. Microbiol. 2:143-149.
Mul et al., 2011, Melanocortin Receptor 4 Deficiency Affects Body Weight Regulation, Grooming Behavior, and Substrate Preference in the Rat, Obesity, 20(3):612-621.
Negrel et al., 1993, Wound-induced tyramine hydroxycinnamoyl transferase in potato (*Solanum tuberosum*) tuber discs, J. Plant Physiol. 142(5):518-524.
Negrel et al., 1995, Induction of phenylpropanoid and tyramine metabolism in pectinase- or pronase-elicited cell suspension cultures of tobacco (*Nicotiana tabacum*). Physiol. Plant. 95:569-574.

(56) References Cited

OTHER PUBLICATIONS

Nelms et al., Aug. 1992, Novel mutations in the pheA gene of *Escherichia coli* K-12 which result in highly feedback inhibition-resistant variants of chorismite mutase/prephenate dehydratase, Appl. Environ. Microbiol. 58(8):2592-2598.

Neuschwander-Tetri et al., 2003, Nonalcoholic Steatohepatitis: Summary of an AASLD Single Topic Conference, Hepatology, 37(5):1202-1219.

Nijkamp et al., 2005, The solvent-tolerant Pseudomonas putida S12 as host for the production of cinnamic acid from glucose, Appl. Microbiol. Biotechnol. 69:170-177.

Nijkamp et al., 2007, Optimization of the solvent-tolerant Pseudomonas putida S12 as host for the production of p-courarate from glucose, Appl. Microbiol. Biotechnol. 74:617-624.

Nishioka et al., 1997, Isolation and activity of N-p-coumaroyltyramine, an a—Jlucosidase inhibitor in welsh onion (*Allium fislulosum*), Biosci. Biotechnol. Biochem. 61(7):1138-1141.

Ogata et al., 1967, Metabolism of aromatic amino acid in microorganisms, Agric. Biol. Chem. 31(2):200-206.

Okayasu et al., 1990, A Novel Method in the Induction of Reliable Experimental Acute and Chronic Ulcerative Colitis in Mice, Gastroenterology, 98(3):694-702.

Olson et al., 2007, Production of tyrosine from sucrose or glucose achieved by rapid genetic changes to phenylalanine-producing *Escherichia coli* strains, Appl. Microbiol. Biotechnol. 74(5):1031-1040.

Palva et al., 1984, lacZ fusions to genes that specify exported proteins: a general technique, Nol. Gen Genet, 194:388-394.

Park et al., 2009, Endosperm-specific expression of tyramine N-hyroxycinnamoyltransferase and tyrosine decarboxylase from a single self-processing polypeptide produces high levels of tyramine derivatives in rice seeds, Biotechnol. Lett. 31(6):911-915.

Park, 2007, Caffedymine from cocoa has cox inhibitory activity suppressing the expression of a platelet activation marker, P-selectin, J. Agric. Food Chem, 55:2171-2175.

Parviz et al., 2003, Hepatocyte Nuclear Factor 4alpha Controls the Development of a Hepatic Epithelium and Liver Morphogenesis, Nature Genetics, 34(3):292-296.

Patnaik et al., Nov. 1994, Engineering of *Escherichia coli* central metabolism for aromatic metabolite production with near theoretical yield, Appl. Environ. Microbiol., 60(11):3903-3908.

Peddibhotla et al., 2013, Discovery of ML314, a Brain Penetrant Nonpeptidio β-Arrestin Biased Agonist of the Neurotensin NTR1 Receptor, ACS Medicinal Chemistry Letters, 4(9):pp. 846-851.

Porter et al., 1999, Functional characterization of agonists at recombinant human 5-HT2A, 5-HT2B and 5-HT2C receptors in CHO-K1 cells, Br J. Pharmacol. 128(1):13-20.

PubChem-CID-88222313, Create Date: Feb. 12, 2015, 9 pp.

PubChem-pccompound-CID 54408305, Create Date Dec. 4, 2011, pp. 1-24.

PubChem-pccompound-selected items 1-14, Create Date Mar. 26, 2005 to Aug. 6, 2016, 3 pp.

Qin et al., 2018, An obesity-associated gut microbiome reprograms the intestinal epigenome and leads to altered colonic gene expression, Genome Biol. 19:7.

Rodriguez et al., 2015, Establishment of a yeast platform strain for production of p-coumaric acid through metabolic enGineering of aromatic amino acid biosynthsis, MetAbolic Engineering, 31:181-188.

Rogers et al., 1984, Meal Patterns and Food Selection During the Development of Obesity in Rats Fed a Cafeteria Diet, Neuroscience & Biobehavioral Reviews, 8(4):441-453.

Roje et al., Feb. 8, 2002, Metabolic engineering in yeast demonstrates that S-adenosylmethionine controls flux through the methylenetetrahydrofolate reductase reaction in vivo, J. Biol. Chem. 277:4056-4061.

Rosler et al., 1997, Maise phenylalanine ammonia-lyase has tyrosine ammonia-lyase activity, Plant Physiol. 113:175-179.

Sambrook et al., 1989, Molecular Cloning: A Laboratory Manual, 2nd ed., Cold Spring Harbor Laboratory, Cold Spring Harbor, NY (TOC).

Sanders et al., 2016, De Novo Lipogenesis in the Liver in Health and Disease: More Than just a Shunting Yard for Glucose, Biological reviews of the Cambridge Philosophical Society, 91(2):452-468.

Savage, 2009, Mouse Models of Inherited Lipodystrophy, Disease Models & Mechanisms, 2(11-12):554-562, (2009).

Schmidt et al., 1998, Elicitor-stimulated biosynthesis of hydroxycinnamoyltyramines in cell suspension cultures of Solanum tuberosum, Planta, 205:51-55.

Schmidt et al., Feb. 12, 1999, Cloning and expression of a potato cDNA encoding hydroxycinnamoyl-CoA:Tyramine N-(Hydroxycinnamoyl)transferase, J. Biol. Chem. 274(7):4273-4280.

Schmidt et al., Mar. 21, 2014, Assessment of constituents inAlliumby multivarate data analysis, high-resolution α-glucosidase inhibition assay and HPLC-SPE, Food Chemistry, 161:192-198.

Shepherd et al., 1993, Adipose Cell Hyperplasia and Enhanced Glucose Disposal in Transgenic Mice Overexpressing GLUT4 Selectively in Adipose Tissue, Journal of Biological Chemistry, 268:.22243-22246.

Shiota et al., 2012, Diabetes in Zucker Diabetic Fatty Rat, Methods in Molecular Biology, 933:103-123.

Sim et al., 2015, Bacterial synthesis of N-hydroxycinnamoyl phenethylamines and tyramines. Microbial Cell Fact. 14:162.

Spath et al., 1998, Hepatocyte Nuclear Factor 4 Provokes Expression of Epithelial Marker Genes, Acting As a Morphogen in Dedifferentiated Hepatoma Cells, Journal of Cell Biology, 140(4):935-946.

Spee et al., 1993, Efficient random mutagenesis method with adjustable mutation frequency by use of PCR and dITP, Nucl. Acids Res. 21(3):777-778.

Sprenger et al., 2007, From scratch to value: engineering *Escherichia coli* wild type cells to the production of L-phenylalanine and other fine chemicals derived from chorismate, Appl. Microbial. Biotechnol. 75:739-749.

Stenman et al., 2012, High-Fat-Induced Intestinal Permeability Dysfunction Associated with Altered Fecal Bile Acids, World Journal of Gastroenterology, 18(9):923-929.

Tatarko et al., 2001, Disruption of a global regulatory gene to enhance central carbon flux into phenylalanine biosynthesis in *Escherichia coli*, Curr. Microbiol. 43:26-32.

Traini et al., 2016, Changes of Excitatory and Inhibitory Neurotransmitters in the Colon of Rats Underwent to the Wrap Partial Restraint Stress, Neurogastroenterology & Motility, 28(8):1172-1185.

Traini et al., 2017, Repeated Otilonium Bromide Administration Prevents Neurotransmitter Changes in Colon of Rats Underwent to Wrap Restraint Stress, Journal of Cellular and Molecular Medicine, 21:735-745.

Trenchard et al., 2015, De novo production of the key branch point benzylisoquinoline alkaloid reticuline in yeast, Metab. Eng. 31:74-83.

Tschop et al., 2001, Rodent Obesity Models: An Overview. Experimental and Clinical Endocrinology & Diabetes, 109(6)307-319.

Villegas et al., 1990, Elicitor-induced hydroxycinnamoyl-CoA:tyramine hydroxycinnamoyltransferase in plant cell suspension cultures, Physiol. Plant. 78:414-420.

Wang et al., 2014, Leptin- and Leptin Receptor-Deficient Rodent Models: Relevance for Human Type 2 Diabetes, Current Diabetes Reports, 10(2):131-145.

Wang et al., 2017, Identification and Quantification of Potential Anti-inflammatory Hydroxycinnamic Acid Amides from Wolfberry, Journal of Agricultural and Food Chemistry, 65:364-372.

Wang et al., Mar. 25, 1994, Functional characterization of a unique liver gene promoter, J. Biol. Chem. 269(12):9137-9146.

Williams et at., 1988, Stress-Induced Changes in Intestinal Transit in the Rat: A Model for irritable Bowel Syndrome, Gastroenterology, 94(3):611-621.

Yakandawala et al., 2008, Metabolic engineering of *Escherichia coli* to enhance phenylalanine production, Appl. Microbiol. Biotechnol. 78:283-291.

(56) References Cited

OTHER PUBLICATIONS

Yamamoto et al., 1994, Effective Production of Glycosyl-Steviosides by Alpha-1,6 Transglucosylation of Dextrin Dextranase, Bioscience, Biotechnology, and Biochemistry, 58(9):1657-1661.

Yaswen et al., 1999, Obesity in the Mouse Model of Pro-Opiomelanocortin Deficiency Responds to Peripheral Melanocortin, Nature Medicine, 5(9):1066-1070.

Yeh, Aug. 2004, C-reactive Protein is an Essential Aspect of Cardiovascular Risk Factor Stratification, The Canadian Journal of Cardiology, 20(Suppl B):93B-96B.

Yi et al., 2003, Altered glucose transport and shikimate pathway product yields in *E. coli*, Biotechnol. Prog. 19:1450-1459.

Yin et al., Hepatic HNF4α is Essential for Maintaining Triglyceride and Cholesterol Homeostasis, Arteriosclerosis, Thrombosis, and Vascular Biology, 31(2, pp. 328-336, (2011).

Zacares et al., 2007, Induction of p-Coumaroyldopamine and feruloyldopamine, two novel metabolites, in tomato by the bacterial pathogen Pseudomonas syringae, Mol. Plant Microbe Interact. 20(11):1439-1448.

Zhao et al., Feb. 1994, Pseudomonas aeruginosa possesses homologues of mammalian phenylalanine hydroxylase and 4α-carbinolamine dehydratase/DCoH as part of a three-component gene cluster, Proc. Natl. Acad. Sci. USA. 91:1366-1370.

Zhou et al., 1991, Random mutagenesis of gene-sized DNA molecules by use of PCR with Taq DNA polymerase, Nucleic Acids Res. 19(21):6052-6052.

Cai et al., "Peptide deformylase is a potential target for anti-Helicobacter pylori drugs: Reverse docking, enzymatic assay, and X-ray crystallography validation", Protein Science, 2006, vol. 15, pp. 2071-2081.

PubChem-CID-88222313, Create Date: Feb. 12, 2015 (Feb. 12, 2015) p. 2.

International Search Report and Written Opinion, dated Dec. 18, 2020, 17 pages.

* cited by examiner

METHOD FOR IMPROVING DIGESTIVE HEALTH

RELATED APPLICATIONS

This application is a continuation of PCT/US2020/043753 filed Jul. 27, 2020, which claims the priority benefit of U.S. Provisional Application No. 62/879,727 filed Jul. 29, 2019, the entire content of each of which is hereby incorporated by reference herein in its entirety.

BACKGROUND

HNF4α is a nuclear receptor that acts as a transcriptional regulator of many genetic programs in humans, including those underlying sugar and lipid metabolism. It is expressed in a number of tissues including the liver, pancreas, and kidney, as well as the intestine. HNF4α is known to have a diverse role in epithelial biology, cells, including the central regulation architecture of epithelial morphogenesis, and homeostasis and barrier functioning of the intestinal epithelium (Cattin, et al. (2009) *Mol. Cell. Biol.* 29(23):6294-6308; Spath & Weiss (1998) *J. Cell Biol.* 140: 935-946). In addition, the HNF4α gene is highly expressed in the small intestine and colon and the HNF4α protein is abundant in the nucleus of mucosal epithelial cells (Jiang, et al. (2003) Nucl. Recept. 1:5). Further, it has been suggested that HNF4α has a protective role in inflammatory bowel disease (IBD), and that HNF4α agonists may be of use in the treatment of IBD (Chahar, et al. (2014) Mol. Cell. Biol. 34:3291-3304).

Studies have shown that HNF4α is critical to the expression and proper localization of tight and adherens junction proteins (Chiba, et al. (2003) *Exp. Cell Res.* 286:288-297; Parviz, et al. (2003) *Nat. Genet.* 34:292-296), and the formation of microvilli within the intestine (Chiba, et al. (2006) *J. Cell Biol.* 175(6):971-980). Further, HNF4α has also been described as a central regulator protecting the intestinal epithelium against inflammation (Babeu & Boudreau (2014) *World J. Gastroenterol.* 20(1):22-30). Moreover, HNF4α expression has been shown to be drastically reduced in intestinal tissues from patients with Crohn's disease (CD) and ulcerative colitis (UC) (Darsigny, et al. (2009) *PLoS One* 4:e7609; Ahn, et al. (2008) *Inflamm. Bowel Dis.* 14:908-920).

Studies with intestine-specific HNF4α null mice have shown that the null mice are more susceptible to dextran sulfate sodium (DSS)-induced colitis, and exhibit an increase in intestinal permeability compared to control mice (Ahn, et al. (2008) *Inflamm. Bowel Dis.* 14: 908-920). In another study, mice lacking intestinal expression of both HNF4α P1 and P2 isoforms developed progressive, chronic gut inflammation similar to human IBD, suggesting that long-term reduction of HNF4α activity is likely to promote IBD (Darsigny, et al. (2009) *PLoS One* 4:e7609).

It is estimated that three million US adults have received the IBD diagnosis, equaling just over 1% of the population, and prevalence is increasing. Direct treatment costs for IBD are estimated to be near $7 billion. Given that many conditions go undiagnosed and IBD can also afflict children, it is likely that the actual prevalence of IBD is much higher and exceeds current cost estimates. Accordingly, there is a need in the art to improve the digestive health of these individuals in a manner which has a high acceptance by patients, efficacy, relative safety, and relatively low cost. The present disclosure addresses this need in the art.

SUMMARY OF THE DISCLOSURE

The present disclosure provides a method for improving digestive health by providing a consumable composition composed of at least one carrier and an effective amount of an extract comprising a compound of Formula I, or an isomer, salt, homodimer, heterodimer, or conjugate thereof:

Formula (I)

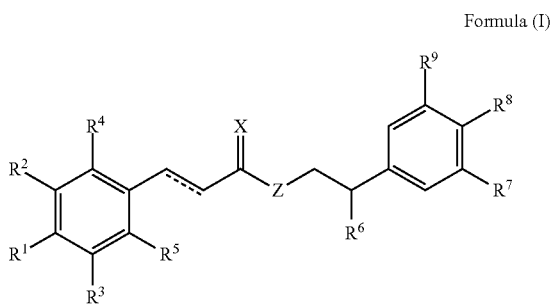

In some embodiments, $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl-$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl; the dashed bond is present or absent; X is $CH_2$ or O; Z is $CHR^a$, $NR^a$, or O; and $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-2}$heteroaryl, thereby improving digestive health.

In some embodiments, the compound has the structure of Formula II:

Formula (II)

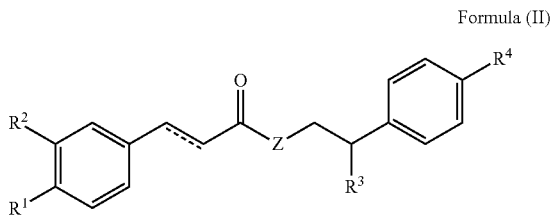

In some embodiments, $R^1$, $R^2$, $R^3$, and $R^4$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl $C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl; the dashed bond is present or absent; Z is CHR$^a$, NR$^a$, or O; and R$^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O) $C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl.

In some embodiments, the extract is an ethanol extract of a member of the genus *Allium, Amoracia, Chenopodium, Spinacia, Fagopyrum, Annona, Jatropha, Hibiscus, Piper, Eragrostis, Zea, Nelumbo, Cannabis, Ziziphus, Zanthoxylum, Ipomea, Capsicum, Lycium, Solanum*, or *Tribulus*.

In some embodiments, the composition is formulated as a dietary supplement, food ingredient or additive, a medical food, nutraceutical or pharmaceutical composition.

In some embodiments, the compound of Formula (I) or Formula (II) is selected from the group consisting of: N-trans-caffeoyltyramine, N-cis-caffeoyltyramine, N-trans-feruloyltyramine, N-cis-feruloyltyramine, p-coumaroyltyramine, cinnamoyltyramine, sinapoyltyramine, and 5-hydroxyferuloyltyramine, or a pharmaceutically acceptable salt, solvates, and combinations of the foregoing.

In some embodiments, the compound of Formula (I) or Formula (II) is selected from the group consisting of: a compound of Formula (II) is selected from (E)-3-(3,4-dihydroxyphenyl)-N-(4-ethoxyphenethyl)acrylamide, (E)-3-(3,4-dihydroxyphenyl)-N-(4-(2-methoxyethoxy)phenethyl)acrylamide, (E)-3-(3,4-dihydroxyphenyl)-N-(4-(2-(methylsulfonyl)ethoxy)phenethyl)acrylamide, (E)-2-(4-(2-(3-(3,4-dihydroxyphenyl)acrylamido)ethyl)phenoxy)acetic acid, ethyl (E)-2-(4-(2-(3-(3,4-dihydroxyphenyl)acrylamido)ethyl)phenoxy)acetate, (E)-N-(4-(cyclopropylmethoxy)phenethyl)-3-(3,4-dihydroxyphenyl)acrylamide, (E)-3-(3,4-dihydroxyphenyl)-N-(4-(3,3,3-trifluoropropoxy) phenethyl)acrylamide, (E)-3-(3,4-dihydroxyphenyl)-N-(4-((tetrahydro-2H-pyran-4yl)methoxy)phenethyl)acrylamide, (E)-3-(3,4-dihydroxyphenyl)-N-(4-((4-fluorobenzyl)oxy) phenethyl)acrylamide, (E)-N-(4-(cyanomethoxy)phenethyl)-3-(3,4-dihydroxyphenyl)acrylamide, (E)-3-(3,4-dihydroxyphenyl)-N-(4-(pyridin-3-ylmethoxy)phenethyl) acrylamide, (E)-3-(3,4-dihydroxyphenyl)-N-(4-(pyridin-2-ylmethoxy)phenethyl)acrylamide, (E)-3-(3,4-dihydroxyphenyl)-N-(4-(2-(dimethylamino)ethoxy) phenethyl)acrylamide, (E)-3-(3,4-dihydroxyphenyl)-N-(4-isobutoxyphenethyl)acrylamide, (E)-3-(3,4-dihydroxyphenyl)-N-(4-(pyridin-4-ylmethoxy)phenethyl) acrylamide, (E)-3-(3,4-dihydroxyphenyl)-N-(4-((4-methoxybenzyl)oxy)phenethyl)acrylamide, (E)-3-(3,4-dihydroxyphenyl)-N-(4-(oxetan-3-ylmethoxy)phenethyl) acrylamide, (E)-3-(3,4-dihydroxyphenyl)-N-(4-((tetrahydro-2H-pyran-2-yl)methoxy)phenethyl) acrylamide, (E)-3-(3,4-dihydroxyphenyl)-N-(4-((tetrahydrofuran-2-yl)methoxy)phenethyl)acrylamide, (E)-3-(3,4-dihydroxyphenyl)-N-(4-(thiophen-2-yloxy) phenethyl)acrylamide, (E)-3-(3,4-dihydroxyphenyl)-N-(4-(3,3-dimethylbutoxy)phenethyl)acrylamide, (E)-3-(3,4-dihydroxyphenyl)-N-(4-(2-hydroxyethoxy)phenethyl) acrylamide, (E)-N-(4-((1H-tetrazol-5-yl)methoxy) phenethyl)-3-(3,4-dihydroxyphenyl)acrylamide, (E)-3-(3,4-dihydroxyphenyl)-N-(4-((1-methylpyrrolidin-2-yl) methoxy)phenethyl)acrylamide, (E)-2-hydroxy-5-(3-((4-hydroxyphenethyl)amino)-3-oxoprop-1-en-1-yl)phenyl hydrogen carbonate, (E)-3-(4-hydroxy-3-(pyridin-4-yloxy) phenyl)-N-(4-hydroxyphenethyl)acrylamide, (E)-3-(4-hydroxy-3-isobutoxyphenyl)-N-(4-hydroxyphenethyl)acrylamide, (E)-3-(3-(4-fluorophenoxy)-4-hydroxyphenyl)-N-(4-hydroxyphenethyl)acrylamide, (E)-3-(3-(cyanomethoxy)-4-hydroxyphenyl)-N-(4-hydroxyphenethyl)acrylamide, (E)-2-(2-hydroxy-4-(3-((4-hydroxyphenethyl)amino)-3-oxoprop-1-en-1-yl)phenoxy)acetic acid, (E)-3-(3-hydroxy-4-(pyridin-4-ylmethoxy)phenyl)-N-(4-hydroxyphenethyl) acrylamide, (E)-3-(4-((4-fluorobenzyl)oxy)-3-hydroxyphenyl)-N-(4-hydroxyphenethyl)acrylamide, (E)-3-(3-hydroxy-4-isobutoxyphenyl)-N-(4-hydroxyphenethyl) acrylamide, (E)-3-(4-(cyanomethoxy)-3-hydroxyphenyl)-N-(4-hydroxyphenethyl)acrylamide, (E)-N-(3-(3,4-dihydroxyphenyl)acryloyl)-N-(4-hydroxyphenethyl) glycine, (E)-3-(3,4-dihydroxyphenyl)-N-(4-hydroxyphenethyl)-N-(pyridin-4-ylmethyl)acrylamide, (E)-3-(3,4-dihydroxyphenyl)-N-(4-hydroxyphenethyl)-N-isobutylacrylamide, (E)-N-(cyanomethyl)-3-(3,4-dihydroxyphenyl)-N-(4-hydroxyphenethyl)acrylamide, 3-(3,4-dihydroxyphenyl)-N-(4-hydroxyphenethyl)propanamide, 3-(3,4-dihydroxyphenyl)-N-(4-(methylsulfonamido) phenethyl)propanamide, or pharmaceutical salts, solvates, and combination of the foregoing.

In some embodiments, the composition of Formula (I) or Formula (II) is in a unit dosage form and is configured for administration between 0.1 and 100 mg/kg of the body weight of the subject per administration.

In some embodiments, administering the compound of Formula (I) or Formula (II) increases HNF4α expression.

In some embodiments, administering the compound of Formula (I) or Formula (II) reverses the loss of Paneth cells that occur from a high fat diet.

In some aspects, a method of treating or preventing a disease or disorder in a subject, comprising: administering a therapeutically effective amount of a compound of Formula I, or a pharmaceutically acceptable salt, to a subject in need thereof, Formula (I)

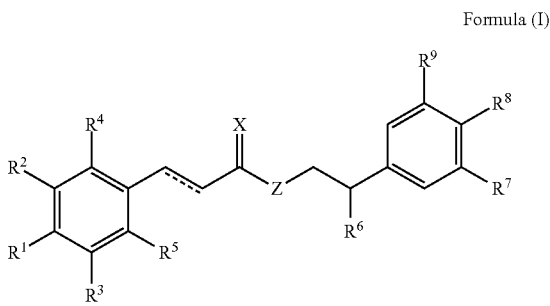

wherein, $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl; the dashed bond is present or absent; X is $CH_2$ or O; Z is $CHR^a$, $NR^a$, or O; and $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl; wherein the disease or disorder is associated with the intestines.

In some embodiments, administering a compound of Formula (I) induces a large increase in HNF4α.

In some embodiments, administering a compound of Formula (I) increases intestinal villus.

In some embodiments, administering a compound of Formula (I) increases Paneth cell formation.

In some embodiments, the disease or disorder associated with the liver or intestines is inflammation.

In some embodiments, the disease or disorder associated with the intestines is a condition associated with an allergic response.

BRIEF DESCRIPTION OF THE DRAWINGS

The features and advantages of the compositions and methods described herein will become apparent from the following description, taken in conjunction with the accompanying drawings. These drawings depict certain aspects of the compositions and methods described in the present application, and thus, are not to be considered limiting. In the drawings, similar reference numbers or symbols typically identify similar components, unless context dictates otherwise. The drawings may not be drawn to scale.

DETAILED DESCRIPTION

Figure 1:
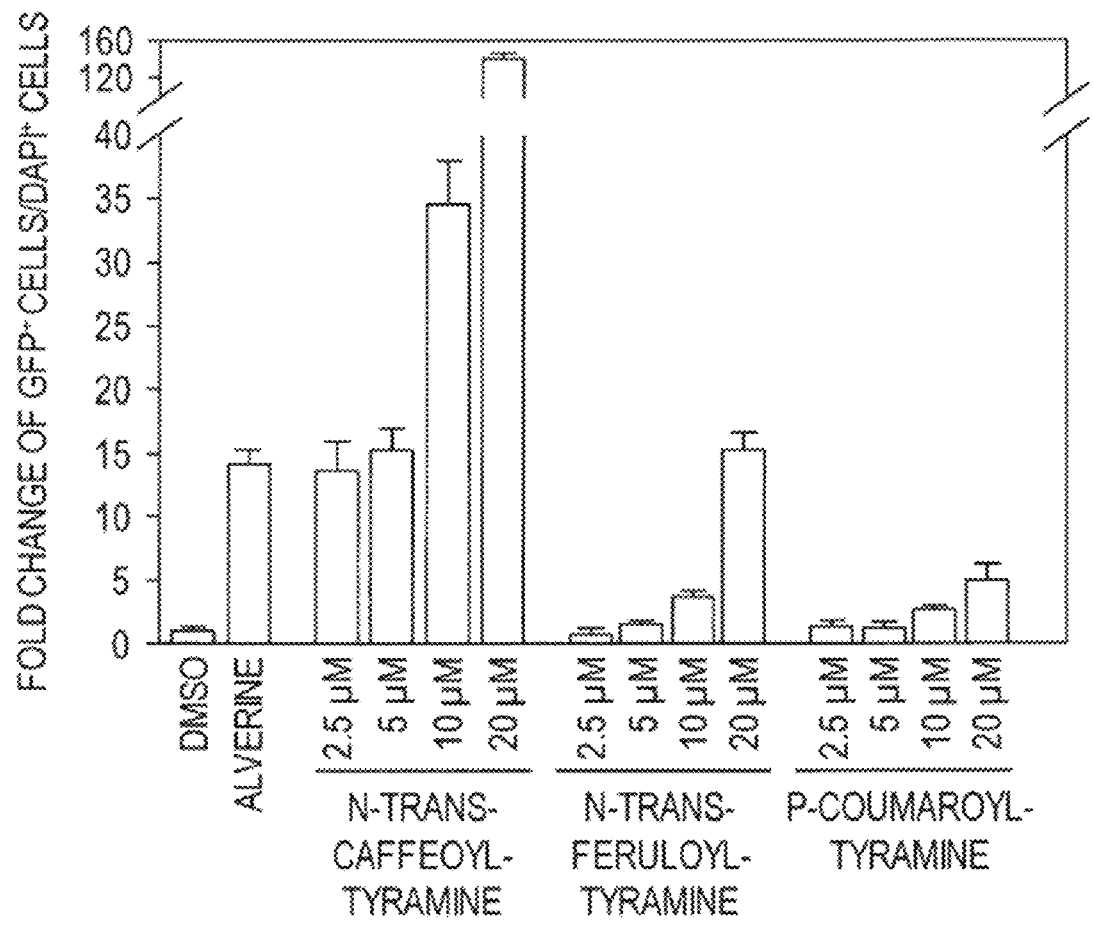
FIG. 1 illustrates a dose-response analysis of N-trans-caffeoyltyramine, N-trans-feruloyltyramine and p-coumaroyltyramine in an assay measuring insulin promoter activity. Dimethylsulfoxide (DMSO) and alverine (20 μM) were used as negative and positive controls, respectively.

It has now been shown that tyramine containing hydroxycinnamic acid amides and extracts containing the same, which are isolated from natural sources, increase or enhance HNF4α expression/activity. Given that decreased expression of HNF4α within the intestinal epithelial layer has been shown to be associated with IBD pathogenesis and other chronic conditions linked to gut inflammation, these natural compounds and extracts are of use in restoring digestive health in IBD and other chronic gastrointestinal conditions. Advantageously, the compounds and extracts of this disclosure have a number of potential benefits including acceptance by patients, relative safety, low cost and use as a complementary approach to conventional Western medicine approaches.

The tyramine containing hydroxycinnamic acid amide of this disclosure are analogs of lead compounds identified in traditional screening assays for agents that modulate known signaling pathways. The tyramine containing hydroxycinnamic acid amides exhibit dose-response HNF4α activity, as initially determined in a T6PNE engineered pancreatic cell, and increase HNF4α mRNA levels. While not wishing to be bound by theory, it is believed that the tyramine containing hydroxycinnamic acid amides of this disclosure increase HNF4α activity as a result of higher affinity for the HNF4α binding site than the natural ligand, palmitic acid, which down regulates HNF4α activity. Accordingly, by increasing HNF4α activity, the compounds of this disclosure are of use in improving heal thy digestive function, thereby addressing the underlying pathogenesis of gastrointestinal disorders such as IBD, UC, and CD. Using the composition of this disclosure, health and well-being are improved and promoted.

Compositions

In some aspects, the disclosure provided herein disclosure provides plant-derived aromatic metabolites with one or more acidic hydroxyl groups attached to aromatic arenes, and their use in modulating metabolism. In one embodiment, the plant-derived aromatic metabolite is a structural analog of compound 1:

Compound 1

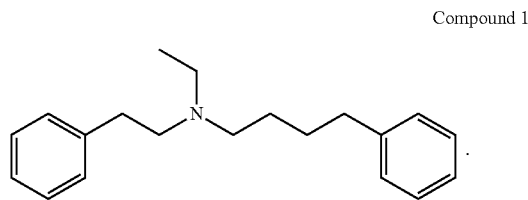 [SMILES: CCN(CCCCc1ccccc1)CCc1ccccc1]

In particular, the disclosure encompasses a compound of Formula (I), or an isomer, salt, homodimer, heterodimer, or conjugate thereof:

Formula (I)

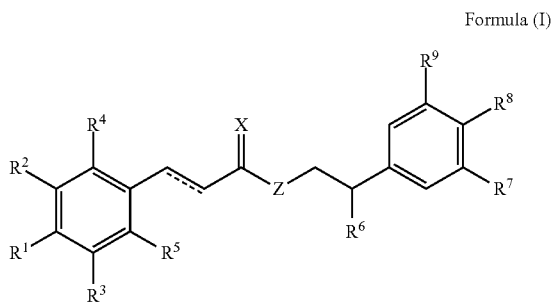

In some embodiments, $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl.

In some embodiments, $R^1$, $R^2$, $R^3$, and $R^8$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl, and $R^4$, $R^5$, $R^6$, $R^7$, and $R^9$ are each independently hydrogen, deuterium, hydroxyl, or halogen;

In some embodiments, $R^1$, $R^2$, and $R^8$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl, and $R^3$, $R^4$, $R^5$, $R^6$, $R^7$, and $R^9$ are each independently hydrogen, deuterium, hydroxyl, or halogen.

In some embodiments, the dashed bond is present or absent.

In some embodiments, X is $CH_2$ or O.

In some embodiments, Z is $CHR^a$, $NR^a$, or O.

In some embodiments, $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl.

In some embodiments, a compound of Formula (I) is provided as a pharmaceutically acceptable salt or solvate thereof.

In some embodiments, a compound of Formula (I) is selected from (E)-3-(3,4-dihydroxyphenyl)-N-(4-ethoxyphenethyl)acrylamide, (E)-3-(3,4-dihydroxyphenyl)-N-(4-(2-methoxyethoxy)phenethyl)acrylamide, (E)-3-(3,4-dihydroxyphenyl)-N-(4-(2-(methylsulfonyl)ethoxy)phenethyl) acrylamide, (E)-2-(4-(2-(3-(3,4-dihydroxyphenyl) acrylamido)ethyl)phenoxy) acetic acid, ethyl (E)-2-(4-(2-(3-(3,4-dihydroxyphenyl)acrylamido)ethyl)phenoxy)acetate, (E)-N-(4-(cyclopropylmethoxy)phenethyl)-3-(3,4-dihydroxyphenyl)acrylamide, (E)-3-(3,4-dihydroxyphenyl)-N-(4-(3,3,3-trifluoropropoxy)phenethyl)acrylamide, (E)-3-(3,4-dihydroxyphenyl)-N-(4-((tetrahydro-2H-pyran-4-yl) methoxy)phenethyl)acrylamide, (E)-3-(3,4-dihydroxyphenyl)-N-(4-((4-fluorobenzyl)oxy)phenethyl) acrylamide, (E)-N-(4-(cyanomethoxy)phenethyl)-3-(3,4-dihydroxyphenyl)acrylamide, (E)-3-(3,4-dihydroxyphenyl)-N-(4-(pyridin-3-ylmethoxy)phenethyl)acrylamide, (E)-3-(3,4-dihydroxyphenyl)-N-(4-(pyridin-2-ylmethoxy)phenethyl) acrylamide, (E)-3-(3,4-dihydroxyphenyl)-N-(4-(2-(dimethylamino)ethoxy)phenethyl)acrylamide, (E)-3-(3,4-dihydroxyphenyl)-N-(4-isobutoxyphenethyl)acryl amide, (E)-3-(3,4-dihydroxyphenyl)-N-(4-(pyridin-4-ylmethoxy) phenethyl)acrylamide, (E)-3-(3,4-dihydroxyphenyl)-N-(4-((4-methoxybenzyl)oxy)phenethyl)acrylamide, (E)-3-(3,4-dihydroxyphenyl)-N-(4-(oxetan-3-ylmethoxy)phenethyl) acrylamide, (E)-3-(3,4-dihydroxyphenyl)-N-(4-((tetrahydro-2H-pyran-2-yl)methoxy)phenethyl) acrylamide, (E)-3-(3,4-dihydroxyphenyl)-N-(4-((tetrahydrofuran-2-yl)methoxy)phenethyl)acrylamide, (E)-3-(3,4- dihydroxyphenyl)-N-(4-(thiophen-2-yloxy)phenethyl) acrylamide, (E)-3-(3,4-dihydroxyphenyl)-N-(4-(3,3-dimethylbutoxy)phenethyl)acrylamide, (E)-3-(3,4-dihydroxyphenyl)-N-(4-(2-hydroxyethoxy)phenethyl)acrylamide, (E)-N-(4-((1H-tetrazol-5-yl)methoxy)phenethyl)-3-(3,4-dihydroxyphenyl)acrylamide, (E)-3-(3,4-dihydroxyphenyl)-N-(4-((1-methylpyrrolidin-2-yl)methoxy)phenethyl)acrylamide, (E)-2-hydroxy-5-(3-((4-hydroxyphenethyl)amino)-3-oxoprop-1-en-1-yl)phenyl hydrogen carbonate, (E)-3-(4-hydroxy-3-(pyridin-4-yloxy)phenyl)-N-(4-hydroxyphenethyl)acrylamide, (E)-3-(4-hydroxy-3-isobutoxyphenyl)-N-(4-hydroxyphenethyl)acrylamide, (E)-3-(3-(4-fluorophenoxy)-4-hydroxyphenyl)-N-(4-hydroxyphenethyl)acrylamide, (E)-3-(3-(cyanomethoxy)-4-hydroxyphenyl)-N-(4-hydroxyphenethyl)acrylamide, (E)-2-(2-hydroxy-4-(3-((4-hydroxyphenethyl)amino)-3-oxoprop-1-en-1-yl)phenoxy)acetic acid, (E)-3-(3-hydroxy-4-(pyridin-4-ylmethoxy)phenyl)-N-(4-hydroxyphenethyl)acrylamide, (E)-3-(4-((4-fluorobenzyl)oxy)-3-hydroxyphenyl)-N-(4-hydroxyphenethyl)acrylamide, (E)-3-(3-hydroxy-4-isobutoxyphenyl)-N-(4-hydroxyphenethyl)acrylamide, (E)-3-(4-(cyanomethoxy)-3-hydroxyphenyl)-N-(4-hydroxyphenethyl)acrylamide, (E)-N-(3-(3,4-dihydroxyphenyl)acryloyl)-N-(4-hydroxyphenethyl)glycine, (E)-3-(3,4-dihydroxyphenyl)-N-(4-hydroxyphenethyl)-N-(pyridin-4-ylmethyl)acrylamide, (E)-3-(3,4-dihydroxyphenyl)-N-(4-hydroxyphenethyl)-N-isobutylacrylamide, (E)-N-(cyanomethyl)-3-(3,4-dihydroxyphenyl)-N-(4-hydroxyphenethyl)acrylamide, 3-(3,4-dihydroxyphenyl)-N-(4-hydroxyphenethyl)propanamide, 3-(3,4-dihydroxyphenyl)-N-(4-(methylsulfonamido)phenethyl)propanamide, or pharmaceutical salts, solvates, and combination of the foregoing.

In some embodiments, the disclosure encloses a compound of Formula (II):

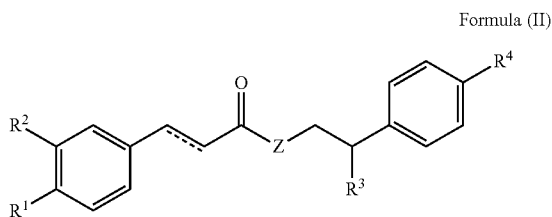

Formula (II)

In some embodiments, $R^1$, $R^2$, $R^3$, and $R^4$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{4-12}$heteroaryl, and optionally substituted —(O)$C_{1-6}$alkyl$C_{1-12}$heteroaryl.

In some embodiments, the dashed bond is present or absent.

In some embodiments, Z is $CHR^a$, $NR^a$, or O.

In some embodiments, $R^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{4-12}$heteroaryl, and optionally substituted —(O)$C_{1-6}$alkyl$C_{1-12}$heteroaryl.

In some embodiments, a compound of Formula (II) is selected from (E)-3-(3,4-dihydroxyphenyl)-N-(4-ethoxyphenethyl)acrylamide, (E)-3-(3,4-dihydroxyphenyl)-N-(4-(2-methoxyethoxy)phenethyl)acrylamide, (E)-3-(3,4-dihydroxyphenyl)-N-(4-(2-(methylsulfonyl)ethoxy)phenethyl)acrylamide, (E)-2-(4-(2-(3-(3,4-dihydroxyphenyl)acrylamido)ethyl)phenoxy)acetic acid, ethyl (E)-2-(4-(2-(3-(3,4-dihydroxyphenyl)acrylamido)ethyl)phenoxy)acetate, (E)-N-(4-(cyclopropylmethoxy)phenethyl)-3-(3,4-dihydroxyphenyl)acrylamide, (E)-3-(3,4-dihydroxyphenyl)-N-(4-(3,3,3-trifluoropropoxy)phenethyl)acrylamide, (E)-3-(3,4-dihydroxyphenyl)-N-(4-((tetrahydro-2H-pyran-4-yl)methoxy)phenethyl)acrylamide, (E)-3-(3,4-dihydroxyphenyl)-N-(4-((4-fluorobenzyl)oxy)phenethyl)acrylamide, (E)-N-(4-(cyanomethoxy)phenethyl)-3-(3,4-dihydroxyphenyl)acrylamide, (E)-3-(3,4-dihydroxyphenyl)-N-(4-(pyridin-3-ylmethoxy)phenethyl)acrylamide, (E)-3-(3,4-dihydroxyphenyl)-N-(4-(pyridin-2-ylmethoxy)phenethyl)acrylamide, (E)-3-(3,4-dihydroxyphenyl)-N-(4-(2-(dimethylamino)ethoxy)phenethyl)acrylamide, (E)-3-(3,4-dihydroxyphenyl)-N-(4-isobutoxyphenethyl)acrylamide, (E)-3-(3,4-dihydroxyphenyl)-N-(4-(pyridin-4-ylmethoxy)phenethyl)acrylamide, (E)-3-(3,4-dihydroxyphenyl)-N-(4-((4-methoxybenzyl)oxy)phenethyl)acrylamide, (E)-3-(3,4-dihydroxyphenyl)-N-(4-(oxetan-3-ylmethoxy)phenethyl)acrylamide, (E)-3-(3,4-dihydroxyphenyl)-N-(4-((tetrahydro-2H-pyran-2-yl)methoxy)phenethyl)acrylamide, (E)-3-(3,4-dihydroxyphenyl)-N-(4-((tetrahydrofuran-2-yl)methoxy)phenethyl)acrylamide, (E)-3-(3,4-dihydroxyphenyl)-N-(4-(thiophen-2-yloxy)phenethyl)acrylamide, (E)-3-(3,4-dihydroxyphenyl)-N-(4-(3,3-dimethylbutoxy)phenethyl)acrylamide, (E)-3-(3,4-dihydroxyphenyl)-N-(4-(2-hydroxyethoxy)phenethyl)acrylamide, (E)-N-(4-((1H-tetrazol-5-yl)methoxy)phenethyl)-3-(3,4-dihydroxyphenyl)acrylamide, (E)-3-(3,4-dihydroxyphenyl)-N-(4-((1-methylpyrrolidin-2-yl)methoxy)phenethyl)acrylamide, (E)-2-hydroxy-5-(3-((4-hydroxyphenethyl)amino)-3-oxoprop-1-en-1-yl)phenyl hydrogen carbonate, (E)-3-(4-hydroxy-3-(pyridin-4-yloxy)phenyl)-N-(4-hydroxyphenethyl)acrylamide, (E)-3-(4-hydroxy-3-isobutoxyphenyl)-N-(4-hydroxyphenethyl)acrylamide, (E)-3-(3-(4-fluorophenoxy)-4-hydroxyphenyl)-N-(4-hydroxyphenethyl)acrylamide, (E)-3-(3-(cyanomethoxy)-4-hydroxyphenyl)-N-(4-hydroxyphenethyl)acrylamide, (E)-2-(2-hydroxy-4-(3-((4-hydroxyphenethyl)amino)-3-oxoprop-1-en-1-yl)phenoxy)acetic acid, (E)-3-(3-hydroxy-4-(pyridin-4-ylmethoxy)phenyl)-N-(4-hydroxyphenethyl)acrylamide, (E)-3-(4-((4-fluorobenzyl)oxy)-3-hydroxyphenyl)-N-(4-hydroxyphenethyl)acrylamide, (E)-3-(3-hydroxy-4-isobutoxyphenyl)-N-(4-hydroxyphenethyl)acrylamide, (E)-3-(4-(cyanomethoxy)-3-hydroxyphenyl)-N-(4-hydroxyphenethyl)acrylamide, (E)-N-(3-(3,4-dihydroxyphenyl)acryloyl)-N-(4-hydroxyphenethyl)glycine, (E)-3-(3,4-dihydroxyphenyl)-N-(4-hydroxyphenethyl)-N-(pyridin-4-ylmethyl)acrylamide, (E)-3-(3,4-dihydroxyphenyl)-N-(4-hydroxyphenethyl)-N-isobutylacrylamide, (E)-N-(cyanomethyl)-3-(3,4- dihydroxyphenyl)-N-(4-hydroxyphenethyl)acrylamide, 3-(3,4-dihydroxyphenyl)-N-(4-hydroxyphenethyl)propanamide, 3-(3,4-dihydroxyphenyl)-N-(4-(methylsulfonamido)phenethyl)propanamide, or pharmaceutical salts, solvates, and combination of the foregoing.

In some embodiments, a compound of Formula (II) is provided as a pharmaceutically acceptable salt or solvate thereof.

In some embodiments, the disclosure encloses a compound of Formula (III):

FORMULA (III)

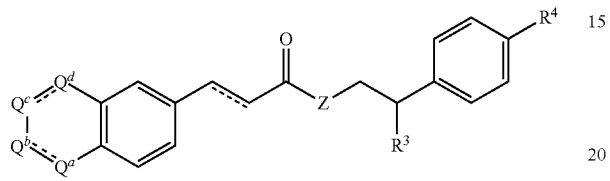

In some embodiments, $R^3$ and $R^4$ are each independently selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl $C_{4-12}$cycloalkyl, optionally substituted —(O)$C_{4-12}$heterocyclyl, optionally substituted —(O)$C_{1-6}$alkyl$C_{2-12}$heterocyclyl, optionally substituted —(O)$C_{5-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl.

In some embodiments, the each independently selected dashed bond is present or absent.

In some embodiments, Z is CHR$^a$, NR$^a$, or O.

In some embodiments, R$^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted —(O)$C_{4-12}$cycloalkyl, optionally substituted —(O)$C_{4-12}$heterocyclyl, optionally substituted —(O)$C_{4-12}$cycloalkyl, optionally substituted —(O)$C_{1-6}$alkyl $C_{5-12}$aryl, optionally substituted —(O)$C_{1-6}$alkyl$C_{5-12}$heteroaryl.

In some embodiments, $Q^a$, $Q^b$, $Q^c$, $Q^d$ are each independently selected from a bond, CHR$^a$, NR$^a$, C═O, and —O—.

In some embodiments, R$^a$ is selected from hydrogen, deuterium, hydroxyl, halogen, cyano, nitro, optionally substituted amino, optionally substituted C-amido, optionally substituted N-amido, optionally substituted ester, optionally substituted —(O)$C_{1-6}$alkyl, optionally substituted —(O)$C_{1-6}$alkenyl, optionally substituted —(O)$C_{1-6}$alkynl, optionally substituted, —(O)$C_{4-12}$cycloalkyl, optionally substituted —(O)$C_{1-6}$alkyl$C_{4-12}$cycloalkyl, optionally substituted —(O)$C_{4-12}$heterocyclyl, optionally substituted —(O)$C_{1-6}$alkyl$C_{4-12}$heterocyclyl, optionally substituted —(O)$C_{4-12}$aryl, optionally substituted —(O)$C_{1-6}$alkyl$C_{5-12}$aryl, optionally substituted —(O)$C_{1-12}$heteroaryl, and optionally substituted —(O)$C_{1-6}$alkyl$C_{1-12}$heteroaryl.

In some embodiments, $Q^c$, $Q^d$ are absent. In some embodiments, $Q^d$ is absent.

In some embodiments, n is 1, 2, 3, or 4

In some embodiments, a compound of Formula (II) is provided as a pharmaceutically acceptable salt or solvate thereof.

"Isomer" refers to especially optical isomers (for example essentially pure enantiomers, essentially pure diastereomers, and mixtures thereof) as well as conformation isomers (i.e., isomers that differ only in their angles of at least one chemical bond), position isomers (particularly tautomers), and geometric isomers (e.g., cis-trans isomers).

In certain embodiments, a compound of Formula (I) or Formula (II) is selected from:

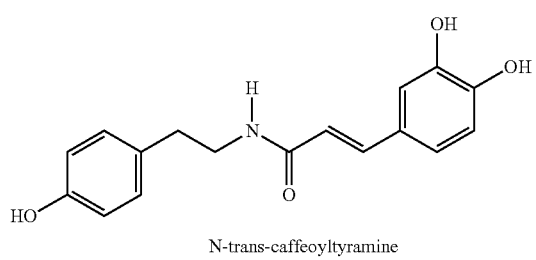

N-trans-caffeoyltyramine

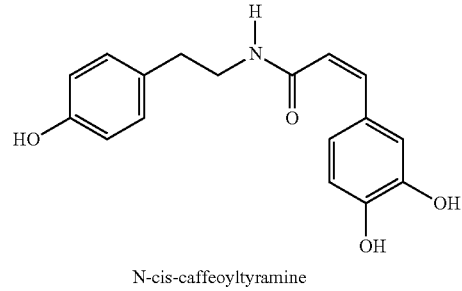

N-cis-caffeoyltyramine

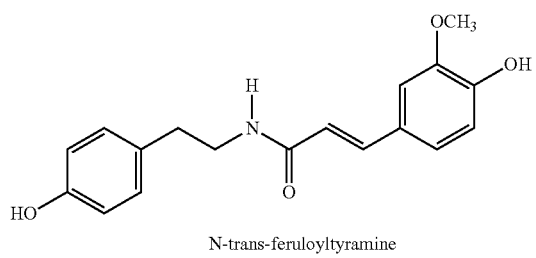

N-trans-feruloyltyramine

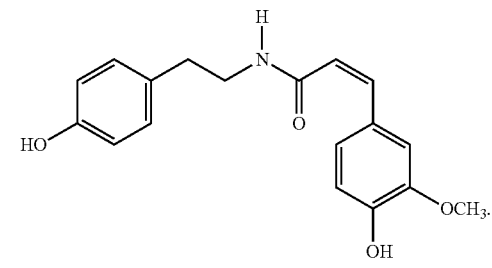

N-cis-feruloyltyramine

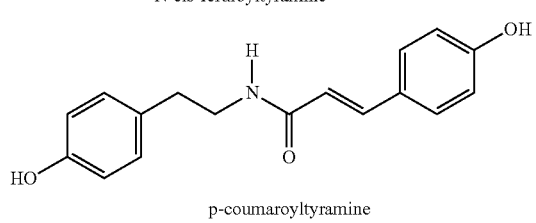

p-coumaroyltyramine

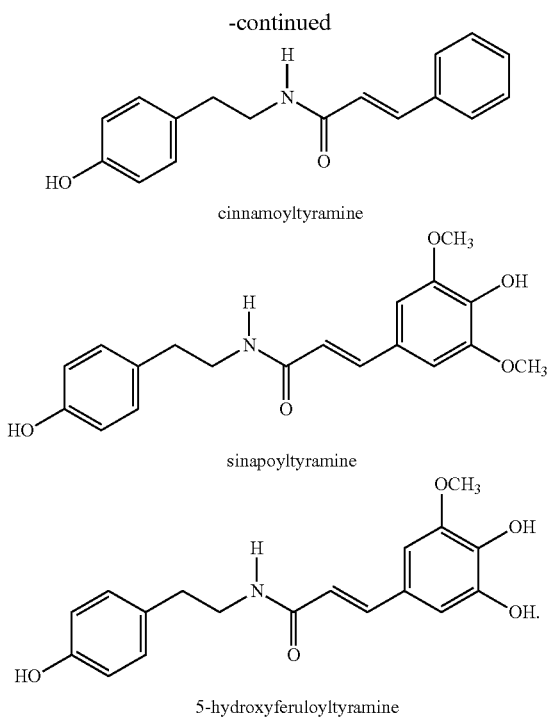

cinnamoyltyramine sinapoyltyramine 5-hydroxyferuloyltyramine

A salt of a compound of this disclosure refers to a compound that possesses the desired pharmacological activity of the parent compound and includes: (1) an acid addition salt, formed with an inorganic acid such as hydrochloric acid, hydrobromic acid, sulfuric acid, nitric acid, phosphoric acid, and the like; or formed with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic camphorsulfonic acid, acid, 4-toluenesulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) a salt formed when an acidic proton present in the parent compound is replaced.

As is known in the art, a homodimer is a molecule composed of two identical tyramine containing hydroxycinnamic acid amide subunits. By comparison, a heterodimer is a molecule composed of two different tyramine containing hydroxycinnamic acid amide subunits. Examples of homodimers of this disclosure include but are not limited to a cross-linked N-trans-feruloyltyramine dimer, a cross-linked N-trans-caffeoyl tyramine dimer and a cross-linked p-coumaroyltyramine dimer. See, for example, King & Calhoun (2005) *Phytochemistry* 66(20): 2468-73, which teaches the isolation of a cross-linked N-transferuloyltyramine dimer from potato common scab lesions.

Conjugates of monomers of tyramine containing hydroxycinnamic acid amide and other compounds, such as lignan amides. Examples of conjugates include, but are not limited to cannabisin A, cannabisin B, cannabisin C, cannabisin D, cannabisin E, cannabisin F and grossamide.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

For the groups herein, the following parenthetical subscripts further define the groups as follows: "($C_n$)" defines the exact number (n) of carbon atoms in the group. For example, "$C_1$-$C_6$-alkyl" designates those alkyl groups having from 1 to 6 carbon atoms (e.g., 1, 2, 3, 4, 5, or 6, or any range derivable therein (e.g., 3-6 carbon atoms)).

In addition to isomers, salts, homodimers, heterodimers, and conjugates, the tyramine containing hydroxycinnamic acid amide may also be glycosylated. A glycosylated tyramine containing hydroxycinnamic acid amide may be produced by transglycosylating the tyramine containing hydroxycinnamic acid amide to add glucose units, for example, one, two, three, four, five, or more than five glucose units, to the tyramine containing hydroxycinnamic acid amide. Transglycosylation can be carried out with any suitable enzyme including, but not limited to, a pullulanase and isomaltase (Lobov, et al. (1991) *Agric. Biol. Chem.* 55:2959-2965), ~-galactosidase (Kitahata, et al. (1989) *Agric. Biol. Chem.* 53:2923-2928), dextrine saccharase (Yamamoto, et al. (1994) *Biosci. Biotech. Biochem.* 58: 1657-1661) or cyclodextrin gluconotransferase, with pullulan, maltose, lactose, partially hydrolyzed starch and maltodextrin being donors.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "C1-C4 alkyl" or similar designations. By way of example only, "C1-C4 alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

The term "halogen atom" or "halogen" as used herein, means any one of the radio-stable atoms of column 7 of the Periodic Table of the Elements, such as chloro (Cl), fluoro (F), bromo (Br) and iodo (I) groups.

In any of the groups described herein, an available hydrogen may be replaced with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, alkoxycarbonyl, acyl, halo, nitro, aryloxycarbonyl, cyano, carboxy, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

As used herein, "alkenyl" refers to an alkyl group, as defined herein, that contains in the straight or branched hydrocarbon chain one or more double bonds. An alkenyl group may be unsubstituted or substituted.

As used herein, "alkynyl" refers to an alkyl group as defined herein, that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to mono- or polycyclic ring systems including at least one heteroatom (e.g., O, N, S). Such systems can be unsaturated, can include some unsaturation, or can contain some aromatic portion, or be all aromatic. A heterocyclyl group can contain from 3 to 30 atoms. A heterocyclyl group may be unsubstituted or substituted.

In particular embodiments, $R^1$ is present and represents a hydroxy group at the para position and $R^2$ is a hydroxy or lower alkoxy group at the meta position. In certain embodiments, the tyramine containing hydroxycinnamic acid amide having the structure of Formula (I) is in the trans configuration.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

The term "amino" as used herein refers to a —$NH_2$ group.

As used herein, the term "hydroxy" refers to a —OH group.

A "cyano" group refers to a "—CN" group.

A "carbonyl" group refers to a C=O group.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-amido may be substituted or unsubstituted.

A "urea" group refers to a "—N($R_A R_B$)—C(=O)—N($R_A R_B$)—" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A urea group may be substituted or unsubstituted.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of some embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of some embodiments can be provided include amorphous forms, milled forms and nano-particulate forms.

Likewise, it is understood that the compounds described herein, such as compounds of some embodiments, include the compound in any of the forms described herein (e.g., pharmaceutically acceptable salts, prodrugs, crystalline forms, amorphous form, solvated forms, enantiomeric forms, tautomeric forms, and the like).

Sources of Active Compound

A compound of this disclosure can be obtained from any suitable botanical species and/or botanical raw material known to possess a compound of Formula (I). Preferably, the compound is provided as an extract comprising the compound or a substantially pure compound.

An "extract" refers to a composition containing a compound of Formula (I), which is separated from other unwanted substances present in the natural source material from which the extract was obtained. In some embodiments, the natural source material is a plant. Plant extracts can be obtained from any plant tissue including a whole plant; a plant part such as shoot vegetative organs/structures (for example, leaves, stems and tubers), roots, flowers and floral organs/structures (for example, bracts, sepals, petals, stamens, carpels, anthers and ovules), a seed (including embryo, endosperm, and seed coat) or fruit (the mature ovary); a plant tissue (for example, vascular tissue, ground tissue, and the like); cells (for example, guard cells, egg cells, and the like), or exudates as well as progeny and cultures or cell lines of the same. Preferably, the extract contains compounds that will be found to be generally recognized as safe (GRAS) for human consumption. Accordingly, in certain embodiments the extract is from an edible source. In this respect, the extract is an edible extract.

Extracts can be prepared by freezing, grinding, macerating, pulverizing, fermenting, percolation, decoction, solvent extraction (e.g., partitioning) or precipitation, treatment with activated charcoal, evaporation, filtration, and/or chromatographic fractionation of the source material of interest. In this respect, an "extract" of the disclosure can be crude, fractionated, sub-fractionated, separated, isolated, enriched or purified, without being limited thereto. The term "crude" means compounds or molecules that have not been entirely separated from the components of the original composition in which it was present. In embodiments pertaining to fractions or sub-fractions, a molecule in crude extract may be subjected to partial separation to provide a less crude extract containing other substances. In some embodiments, the compound is isolated. The term "isolated" means that a compound or molecule is substantially enriched or purified with respect to the complex cellular milieu in which it naturally occurs, such as in a crude extract. When an isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances), which may for example contain other components. In other circumstances, the isolated molecule may be purified to essential homogeneity, for example as determined spectrophotometrically, by NMR or by chromatography (for example LC-MS).

Suitable solvents for preparing an extract include, e.g., n-pentane, hexane, butane, chloroform, dichloromethane, di-ethyl ether, acetonitrile, water, butanol, isopropanol, ethanol, methanol, glacial acetic acid, acetone, butanone, pentanone, norflurane (HFA134a), ethyl acetate, dimethyl sulfoxide, heptafluoropropane (HFA227), and subcritical or supercritical fluids such as liquid carbon dioxide and water, or a combination thereof in any proportion. When solvents such as those listed above are used, the resultant extract typically contains non-specific lipid-soluble material. This can be removed by a variety of processes including "winterization", which involves chilling to a specified temperature, typically −20° C. followed by filtration or centrifugation to remove waxy ballast, extraction with subcritical or supercritical carbon dioxide or non-polar solvents (e.g., hexane) and by distillation.

Extracts enriched for a compound of the disclosure are ideally obtained by chromatographic fractionation. Chromatographic fractionation typically includes column chromatography and may be based on molecular sizing, charge, solubility and/or polarity. Depending on the type of chromatographic method, column chromatography can be carried out with matrix materials composed of, for example, dextran, agarose, polyacrylamide, silica, C18, C8, polyvinylpyrrolidone, polystyrene, celite, and phenyl-hexy and can include solvents such as dimethyl sulfoxide, pyridine, water, dimethylformamide, methanol, saline, ethylene dichloride, chloroform, propanol, ethanol, isobutanol, formamide, methylene dichloride, butanol, acetonitrile, isopropanol, tetrahydrofuran, dioxane, chloroform/dichloromethane, methanol, hexane, and ethyl acetate.

Typically, the product of the chromatographic step is collected in multiple fractions, which may then be tested for the presence of the desired compound using any suitable analytical technique (e.g. thin layer chromatography, mass spectrometry, and ultraviolet absorption). Fractions enriched in the desired compound may then be selected for further purification.

As an alternative, or in conjunction with chromatography, crystallization may be performed to obtain high purity amides. The hydroxycinnamic tyramine solubility containing of the acid amide is hydroxycinnamic acid tyramine adjusted by containing changing temperature and/or the composition of the solution, for instance by removing ethanol, and/or adjusting the pH to facilitate precipitation, followed by filtration or centrifugation of the precipitated crystals or oils. Other suitable methods include, but are not limited to, liquid-liquid extraction, centrifugal partition chromatography or adsorption onto a resin or removal of impurities with resin.

A "substantially pure" preparation of a compound is defined as a preparation having a chromatographic purity (of the desired compound) of greater than 95%, more preferably greater than 96%, more preferably greater than 97%, more preferably greater than 98%, more preferably greater than 99% and most preferably greater than 99.5%, as determined by area normalization of an HPLC profile.

The term "extract comprising a compound" encompasses preparations having at least 2%, preferably greater than 5%, more preferably greater than 10% chromatographic purity for the desired compound. Such an extract will generally contain a greater proportion of impurities, non-target materials and other molecules than a "substantially pure" preparation.

In particular embodiments, an "extract comprising a compound" is a "botanical" product or substance. In this context, "botanical" refers to "products that include plant materials, algae, macroscopic fungi and combinations thereof." Botanicals are defined by the process steps used to prepare the extract (e.g., by pulverization, decoction, expression, aqueous and/or ethanol extraction) and provide a quantified amount of one or more of the compounds of interest.

Ideally, a compound of this disclosure is extracted and/or purified from a plant. Exemplary plants sources include, but are not limited to, plants in the genera, family, order, genus, species listed in Table 1.

TABLE 1

| Order | Family | Genus | Common name |
| --- | --- | --- | --- |
| Asparagales | Amaryllidaceae | Allium | Garlic |
|  |  |  | Onion |
|  |  |  | Leek |
| Barssicales | Barriscaceae | Amoracia | Horseradish |
| Caryophyllales | Amaranthaceae | Chenopodium | Quinoa |
|  |  | Spinacia | Spinach |
| Magnoliales | Annonaceae | Annona | Cherimoya |
|  |  |  | Atemoya |
|  |  |  | Soursop |
|  |  |  | Sweetsop |
|  |  |  | Custard apple |
|  |  |  | Guanabana |
| Malpighiales | Euphorbiaceae | Jatropha | Barbados nut |
| Malvales | Malvaceae | Hibiscus | Hibiscus |
| Piperales | Piperaceae | Piper | Black pepper |
| Poales | Poaceae | Eragrostis | Teff |
|  |  | Zea | Corn |
| Protealese | Nelumbonaceae | Nelumbo | Sacred Lotus |
| Rosales | Cannabaceae | Cannabis | Hemp |
|  |  | Ziziphus | Red date |
|  |  | Lycium | Goji/wolf berry |
| Sapindales | Rutaceae | Zanthoxylum | Szechuan peppercorn |
| Solanales | Convolvulaveae | Ipomea | Sweet potato |
|  | Solanaceae | Capsicum | Serrano pepper |
|  |  |  | Thai Chili |
|  |  |  | Piri piri pepper |
|  |  | Solanum | Tomato |
|  |  |  | Potato |
| Zygophyllaceae | Ophyllales | Tribulus | Goat thorn |
|  |  |  | Puncture vine |

By way of illustration, an extract containing N-trans-caffeoyltyramine is obtained pulverizing the dried fruit of by *Tribulus* grinding or *terrestris*, subjecting the pulverized material to 80% ethanol at room temperature, filtering and concentrating the 80% ethanol extract, resuspending the concentrated extract in water, partitioning the aqueous solution with hexane, adding chloroform to the aqueous layer, and subjecting the chloroform layer to liquid chromatography with silica gel. See, e.g., Ko, et al. (2015) *Internad. J. Mol. Med.* 36(4):1042-8.

An extract containing a tyramine containing hydroxycinnamic acid amide can be standardized using conventional techniques such as high-performance liquid chromatography (HPLC) or high-performance thin-layer chromatography (HPTLC). The term "standardized extract" refers to an extract which is standardized by identifying characteristic ingredient(s) or bioactive marker(s) present in the extract. Characterization can be, for example, by analysis of the spectral data such as mass spectrum (MS), infrared (IR), ultraviolet (UV) and nuclear magnetic resonance (NMR) spectroscopic data.

Biological Activity

Biological activity of compounds and/or extracts can be determined using one or more of the well-known biological assays and animal models described in more detail below. Each of these assays would provide a measure of the activity of the compounds of the present disclosure to provide beneficial effects on cellular endpoints linked to digestive health and chronic intestinal diseases or disorders including but not limited to IBD, irritable bowel syndrome (IBS), UC, celiac disease and CD.

Model of Epithelial Barrier Integrity. To assess barrier function, 3D spheroids are incubated basolaterally with the plasma samples from subjects with IBS or healthy controls. Medium only and 2 mM ethylene glycol tetra-acetic acid (EGTA) ae used as negative and positive controls, respectively. Spheroids are incubated with 2 mL containing 37.5% (v/v) plasma, 52.5% (v/v) medium and 10% (v/v) fluorescein isothiocyanate-labelled dextran of 4 kDa (FD4) in the presence or absence of a compound or extract of this disclosure. The basal to luminal FD4 permeation is assessed by confocal microscopy. See Ludidi, et al. (2015) *PLoS One* 10(5):e0123498.

Enteroid-Derived Polarized Monolayer (EDM)-Monocyte Co-Culture Model. To assess the 3-way interactions between microbes, gut epithelium, and the immune system, an EDM-monocyte EDM-monocyte co-culture model may be used. See WO 2018/161077 A1. In this assay, the EDMs are adapted for coculture in 2 chamber slides with IBD-associated microbes on the apical side and non-epithelial (immune and non-immune cells, e.g., monocytes, T-cells, myofibroblasts, etc.) on the basolateral side to recreate the 3-way system comprising microbes, gut epithelium, and the immune system. The impact of microbes on the epithelium, and the ability of the latter to release soluble factors on the basolateral side (cytokines such as MCP-1 or Butyrophillins, which attract γδ T-cells) can be assessed, alongside the measurement of how such factors trigger the recruitment and activation of non-epithelial cells. Using this approach, the effect of extracts or compounds of the present disclosure on the complex interplay between the gut microbes, the epithelium, and non-epithelial cells can individually be assessed for gene expression by RNA sequencing and cytokine expression by qPCR and ELISAs.

Animal Model of IBS. The Wrap Restrain Stress (WRS) model is an established model for human IBS (Williams, et al. (1988) *Gastroenterology* 94: 611-621). WRS model is commonly applied once (acute test) and includes a forced immobilization of the animal lasting at least for 2 hours. The efficacy of this test is confirmed by the development of an immediate hyperalgesia, quantifiable in colon-rectal distention (CRD) number, the inhibition of small intestinal transit, the stimulation of large intestinal activity and increased fecal excretion. In addition, it has been demonstrated that rats in this assay presented a low-grade mucosal inflammation with a significant increase in mast cells and eosinophylic granulocytes (Traini, et al. (2016) *Neurogastroenterol. Motil.* 28:1172-1185; Traini, et al. (2017) *J. Cell. Mol. Med.* 21:735-745) that overlapped what is described in colonic biopsies of IBS. Moreover, these animals showed important changes in the glial cells, in inhibitory and excitatory neurotransmitters and receptors that were interpreted as responsible for the dysmotility and hypersensitivity present in IBS patients. Such a model is useful for demonstrating in vivo response for compounds of the present disclosure and exploring key concepts such as dose-response.

Animal Model of Chronic Colitis. Chronic coli tis is induced by exposure to 1% to 5% (wt/vol) dextran sodium sulfate (molecular weight 36,000-50,000 kDa) dissolved in drinking water (Okayasu, et al. (1990) *Gastroenterology* 98:694-702). DSS is given ad libitum for five to seven days, followed by several days of normal drinking water. During DSS administration, mice develop an acute colitis with ulcerations, body weight loss, and bloody diarrhea. Therefore, beginning on the day after the third DSS cycle, mice are provided with a compound or extract of this disclosure to demonstrate in vivo response. Macroscopic and histological scores are assessed on the whole colon, while biochemical assays may be performed on colonic segments collected from an inflamed region adjacent and distal to the gross necrotic damage.

Counter Screens. Counter screens are often used to select among a library of compounds in order to avoid off target effects. In the present disclosure, the activity of compounds as modulators of HFN4α activity is the desired target even though other off target effects may occur. Drugs that have been marketed for use in humans based on target effects other than HFN4α have subsequently been shown to have activity as HNF4α activators (Alverine and Benfluorex; Lee, et al. (2013) *ACS Chem. Biol.* 8 (8): 1730-6). Alverine has been marketed as a smooth muscle relaxant for gastrointestinal disorders, while Benfluorex was marketed as an anorectic agent. Benfluorex was known to be metabolized by cleavage of an ester moiety into fenfluramine, a potent agonist of serotonin 5-hydroxytryptamine 2 (5-$HT_2$) receptors, an effect that was thought to be related to its activity as an anorectic agent (Porter, et al. (1999) *Br. J. Pharmacol.* 128 (1):13-20). However, modulation of 5-$HT_2$ receptors by Benfluorex was linked to undesirable cardiopulmonary side effects. Accordingly, based on these experiences with synthetic compounds, compounds and extracts of the present disclosure will be tested for off target effects on 5-hydroxytryptamine receptor activation using, e.g. a fluorometric imaging plate reader (FLIPR) assay, which allows rapid detection of rises in intracellular calcium levels in cells expressing a human 5-$HT_{2A}$, 5-$HT_{2B}$ or 5-$HT_{2C}$ receptor in CHO-K1 cells. See, e.g., Porter, et al. (1999) *Br. J. Pharma col.* 128 (1): 13-20. Other counter screens may be chosen based on initial studies where toxic effects may be linked to other off target actions.

Formulations

A substantially pure compound or extract comprising a compound of this disclosure can be combined with a carrier and provided in any suitable form for consumption by or administration to a subject. In this respect, the compound or extract is added as an exogenous ingredient or additive to the consumable. Suitable consumable forms include, but are not limited to, a dietary supplement, food ingredient or additive, a medical food, nutraceutical or pharmaceutical composition. In some embodiments, the compound or extract is provided in either a liquid or powder form.

A food ingredient or additive is an edible substance intended to result, directly or indirectly, in its becoming a component or otherwise affecting the characteristic of any food (including any substance intended for use in producing, manufacturing, packing, processing, preparing, treating, packaging, transporting, or holding food). A food product, in particular a functional food, is a food fortified or enriched during processing to include additional complementary nutrients and/or beneficial ingredients. A food product according to this disclosure can, e.g., be in the form of butter, margarine, sweet or savory spreads, condiment, biscuits, health bar, bread, cake, cereal, candy, confectionery, soup, milk, yogurt or a fermented milk product, cheese, juice-based and vegetable-based beverages, fermented beverages, shakes, flavored waters, tea, oil, or any other suitable food. In some embodiments, the food product is a whole-food product in which the concentration of the compound has been enriched through particular post-harvest and food production processing methods to levels that provide an efficacious amount of the compound.

A dietary supplement is a product taken by mouth that contains a compound or extract of the disclosure and is intended to supplement the diet. A nutraceutical is a product derived from a food source that provides extra health benefits, in addition to the basic nutritional value found in the food. A pharmaceutical composition is defined as any component of a drug product intended to furnish pharmacological activity or other direct effect in the diagnosis, cure, mitigation, treatment, or prevention of disease, or to affect the structure or any function of the body of humans or other animals. Dietary supplements, nutraceuticals and pharmaceutical compositions can be found in many capsules, forms such as tablets, coated tablets, pills, capsules, pellets, granules, softgels, gelcaps, liquids, powders, emulsions, suspensions, elixirs, syrup, and any other form suitable for use.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound described herein, including a compound of Formula (I), (II), (III), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

The compounds, salt and/or pharmaceutical composition can be provided to an administering physician or other health care professional in the form of a kit. The kit is a package which houses a container which contains the compound(s) in a suitable pharmaceutical composition, and instructions for administering the pharmaceutical composition to a subject. The kit can optionally also contain one or more additional therapeutic agents. The kit can also contain separate doses of a compound(s) or pharmaceutical composition for serial or sequential administration. The kit can optionally contain one or more diagnostic tools and instructions for use. The kit can contain suitable delivery devices, for example, syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject.

In some embodiments, a compound of Formula (I), Formula (II), or Formula (III) is administered at a dose in the range of about 1-200 mg/kg body weight. In some embodiments, a compound of Formula (I), Formula (II), or Formula (III) is administered at a dose in the range of about 1-10, 1-20, 1-30, 1-40, 1-50, 1-60, 1-70, 1-80, 1-90, 1-100, 1-200, 1-300, 1-400, 1-500, 1-600, 1-700, 1-800, 1-900, 1-1000, 1-11, 1-12, 1-13, 1-13, 1-14, 1-15, 1-16, 1-17, 1-18, 1-19, 10-20, 10-30, 10-40, 10-50, 10-60, 10-70, 10-80, 10-90, 10-100, 10-200, 10-300, 10-400, 10-500, 10-600, 10-700, 10-800, 10-900, 10-1000, 20-30, 20-40, 20-50, 20-60, 20-70, 20-80, 20-90, 20-100, 20-200, 20-300, 20-400, 20-500, 20-600, 20-700, 20-800, 20-900, 20-1000, 30-40, 30-50, 30-60, 30-70, 30-80, 30-90, 30-100, 30-200, 30-300, 30-400, 30-500, 30-600, 30-700, 30-800, 30-900, 30-1000, 40-50, 40-60, 40-70, 40-80, 40-90, 40-100, 40-200, 40-300, 40-400, 40-500, 40-600, 40-700, 40-800, 40-900, 40-1000, 50-60, 50-70, 50-80, 50-90, 50-100, 50-200, 50-300, 50-400, 50-500, 50-600, 50-700, 50-800, 50-900, 60-70, 60-80, 60-90, 60-100, 60-200, 60-300, 60-400, 60-500, 60-600, 60-700, 60-800, 60-900, 60-1000, 70-80, 70-90, 70-100, 70-200, 70-300, 70-400, 70-500, 70-600, 70-700, 70-800, 70-900, 70-1000, 80-90, 80-100, 80-200, 80-300, 80-400, 80-500, 80-600, 80-700, 80-800, 80-900, 80-100, 90-100, 90-200, 90-300, 90-400, 90-500, 90-600, 90-700, 90-800, 90-900, 90-1000, 100-150, 100-200, 100-300, 100-400, 100-500, 100-600, 100-700, 100-800, 100-900, or 100-1000 mg/kg of body weight. In some embodiments, a compound of Formula (I), Formula (II), or Formula (III) is administered at a dose of about 0.01, 0.02, 0.03, 0.05, 0.07, 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50, 55, 60, 65, 70, 80, 90, or 95 mg/kg of the body weight. In some embodiments, a compound of Formula (I), Formula (II), or Formula (III) is administered at a dose less than about 0.01, 0.02, 0.03, 0.05, 0.07, 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, a compound of Formula (I), Formula (II), or Formula (III) is administered at a dose greater than about 0.01, 0.02, 0.03, 0.05, 0.07, 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 mg/kg of a subjects body weight.

In some embodiments, a compound of Formula (I), Formula (II), or Formula (III) dose is about 0.1 mg-10 mg, 0.1 mg-25 mg, 0.1 mg-30 mg, 0.1 mg-50 mg, 0.1 mg-75 mg, 0.1 mg-100 mg, 0.5 mg-10 mg, 0.5 mg-25 mg, 0.5 mg-30 mg, 0.5 mg-50 mg, 0.5 mg-75 mg, 0.5 mg-100 mg, 1 mg-10 mg, 1 mg-25 mg, 1 mg-30 mg, 1 mg-50 mg, 1 mg-75 mg, 1 mg-100 mg, 2 mg-10 mg, 2 mg-25 mg, 2 mg-30 mg, 2 mg-50 mg, 2 mg-75 mg, 2 mg-100 mg, 3 mg-10 mg, 3 mg-25 mg, 3 mg-30 mg, 3 mg-50 mg, 3 mg-75 mg, 3 mg-100 mg, 4 mg-100 mg, 5 mg-10 mg, 5 mg-25 mg, 5 mg-30 mg, 5 mg-50 mg, 5 mg-75 mg, 5 mg-300 mg, 5 mg-200 mg, 7.5 mg-15 mg, 7.5 mg-25 mg, 7.5 mg-30 mg, 7.5 mg-50 mg, 7.5 mg-75 mg, 7.5 mg-100 mg, 7.5 mg-200 mg, 10 mg-20 mg, 10 mg-25 mg, 10 mg-50 mg, 10 mg-75 mg, 10 mg-100 mg, 15 mg-30 mg, 15 mg-50 mg, 15 mg-100 mg, 20 mg-20 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, or about 40 mg-60 mg. In some embodiments, a compound of Formula (I), Formula (II), or Formula (III) administered is about 20 mg-60 mg, 27 mg-60 mg, 20 mg-45 mg, or 27 mg-45 mg. In some embodiments, a compound of Formula (I), Formula (II), or Formula (III) administered is about 1 mg-5 mg, 1 mg-7.5 mg, 2.5 mg-5 mg, 2.5 mg-7.5 mg, 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, a compound of Formula (I), Formula (II), or Formula (III) dose is greater than, equal to, or about 0.1 mg, 0.3 mg, 0.5 mg, 0.75 mg, 1 mg, 1.25 mg, 1.5 mg, 1.75 mg, 2 mg, 2.5 mg, 3 mg, 3.5 mg, 4 mg, 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, about 200 mg, about 300 mg. about 400 mg, about 500 mg, about 600 mg, about 700 mg, about 800 mg, about 900 mg, or about 1000 mg. In some embodiments, a compound of Formula (I), Formula (II), or Formula (III) dose is about less than about 0.5 mg, 0.75 mg, 1 mg, 1.25 mg, 1.5 mg, 1.75 mg, 2 mg, 2.5 mg, 3 mg, 3.5 mg, 4 mg, 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

The term "carrier" as used herein means a material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier should be compatible with the other ingredients of the formulation and not injurious to the subject. Some examples of materials that can serve as carriers include: (1) sugars, such as lactose, glucose and sucrose; (2) starches, such as corn starch and potato starch; (3) cellulose, and its derivatives, such as sodium carboxymethyl cellulose, ethyl cellulose, cellulose acetate, and hydroxyl propyl methyl cellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other nontoxic compatible substances employed in conventional formulations.

For preparing solid compositions such as tablets or capsules, the compound or extract is mixed with a carrier (e.g., conventional tableting ingredients such as corn starch, lactose, sucrose, sorbitol, talc, stearic acid, magnesium stearate, dicalcium phosphate or gums) and other diluents (e.g., water) to form a solid composition. This solid composition is then subdivided into unit dosage forms containing an effective amount of the compound of the present disclosure. The tablets or pills containing the compound or extract can be coated or otherwise compounded to provide a dosage form affording the advantage of prolonged action.

In particular embodiments of this disclosure, a consumable composition includes the compound or extract, a carrier and a preservative to reduce or retard microbial growth. The preservative is added in amounts up to about 5%, preferably from about 0.01% to 1% by weight of the film. Preferred preservatives include sodium benzoate, methyl parabens, propyl parabens, sodium nitrite, sulphur dioxide, sodium sorbate and potassium sorbate. Other suitable preservatives include, but are not limited to, salts of edetate, (also known as salts of ethylenediaminetetraacetic acid, or EDTA, such a disodium EDTA).

The liquid forms in which the compound or extract of the disclosure is incorporated for oral or parenteral administration include aqueous solution, suitably flavored syrups, aqueous or oil suspensions, and flavored emulsions with edible oils as well as elixirs and similar vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Liquid preparations for oral administration may take the form of, for example, solutions, syrups or suspensions, or they may be presented as a dry product for reconstitution with water or other suitable vehicles before use. Such liquid preparations may be prepared by conventional means with acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

Methods of preparing formulations or compositions of this disclosure include the step of bringing into association a compound or extract of the present disclosure with the carrier and, optionally, one or more accessory and/or active ingredients. In general, the formulations are prepared by uniformly and intimately bringing into association a compound or extract of the present disclosure with liquid carriers, or finely divided solid carriers, or both, and then, if necessary, shaping the product. As such, the disclosed formulation may consist of, or consist essentially of a compound or extract described herein in combination with a suitable carrier.

When a compound or extract of the present disclosure is administered as pharmaceuticals, nutraceuticals, or dietary supplements to humans and animals, they can be given per se or as a composition containing, for example, 0.1 to 99% (more preferably, 10 to 30%) of active ingredient in combination with an acceptable carrier.

A consumable product may be consumed by a subject to provide less than 100 mg of a compound disclosed herein per day. In certain embodiments, the consumable provides between 10 and 60 mg/day of a tyramine containing hydroxycinnamic acid amide. The effective amount can be established by methods known in the art and be dependent upon bioavailability, toxicity, etc.

While it is contemplated that individual tyramine containing hydroxycinnamic acid amides may be used in the consumables of this disclosure, it is further contemplated that two or more of the compounds or extracts could be combined in any relative amounts to produce custom combinations of ingredients containing two or more tyramine containing hydroxycinnamic acid amides in desired ratios to enhance product efficacy, improve organoleptic properties or some other measure of quality important to the ultimate use of the product.

Molecular Target

HNF4α (hepatocyte nuclear factor 4α) is a global nuclear transcription factor, regulating expression of many genes involved in maintaining balanced metabolism (homeostasis). It is expressed in a number of tissues including the liver, pancreas, and kidney, as well as the intestine. HNF4α is known to have a diverse role in epithelial biology, including the architecture of epithelial cells, central regulation of epithelial morphogenesis, and homeostasis and barrier functioning of the intestinal epithelium (Cattin, et al. (2009) *Mal. Cell. Biol.* 29(23): 6294-6308; Spath & Weiss (1998) *J. Cell Biol.* 140: 935-946). In addition, the HNF4α gene is highly expressed in the small intestine and colon and the HNF4α protein is abundant in the nucleus of mucosal epithelial cells (Jiang, et al. (2003) *Nucl. Recept.* 1:5). Further, it has been suggested that HNF4α has a protective role in IBD, and that HNF4α agonists may be of use in the treatment of IBD (Chahar, et al. (2014) *Mol. Cell. Biol.* 34:3291-3304).

Studies have shown that HNF4α is critical to the expression and proper localization of tight and adherens junction proteins (Chiba, et al. (2003) *Exp. Cell Res.* 286:288-297;

Parviz, et al. (2003) *Nat. Genet.* 34:292-296), and the formation of microvilli within the intestine (Chiba, et al. (2006) *J. Cell Biol.* 175(6): 971-980). Further, HNF4α has also been described as a central regulator protecting the intestinal epithelium against inflammation (Babeu & Boudreau (2014) *World J. Gastroenterol.* 20(1): 22-30). Moreover, HNF4α expression has been shown to be drastically reduced in intestinal tissues from patients with Crohn's disease (CD) or Ulcerative colitis (UC) (Darsigny, et al. (2009) *PLoS One* 4:e7609; Ahn, et al. (2008) *Inflamm. Bowel Dis.* 14:908-920).

Studies with intestine-specific HNF4α null mice have shown that the null mice are prone to increased susceptibility to dextran sulfate sodium (DSS) model of colitis, as well as showed increased intestinal permeability than control mice (Ahn, et al. (2008) *Inflamm. Bowel Dis.* 14:908-920). In another study, mice lacking intestinal expression of both HNF4α P1 and P2 isoforms developed progressive, chronic gut inflammation similar to human IBD, suggesting that long-term reduction of HNF4α activity is likely to promote IBD (Darsigny, et al. (2009) *PLoS One* 4:e7609).

Alternatively, or in addition to, the underlying pathophysiological mechanism for HNF4α's role in regulating gut permeability is that HNF4α may interact with gut microbiota to prevent the development of chronic inflammation. In particular, it has been suggested that HNF4α is a microbial-suppressed transcription factor within the gut, and that the genes governed by this regulation may include factors that could provide new targets for IBD therapy (Davison, et al. (2017)*Genome Res.* 27:1195-206). Further, it has been demonstrated that HNF4α expression is influenced by diet and bacteria. In particular, products of bacterial metabolism within the colon may produce fatty acids that serve as ligands for HNF4α thereby altering its expression (Qin, et al. (2018) *Genome Biol.* 19:7). Moreover, bile acids (or their derivatives), which are also related to intestinal permeability (Stenman, et al. (2012) *World J. Gastroenterol.* 18(9): 923-9), may act as HNF4α ligands.

Clinical evidence further indicates that HNF4α agonists may be beneficial for treatment of digestive disorders and disease. Specifically, the HNF4α agonist Alverine has been approved for use in Europe for treatment of IBS.

Chronic Gastrointestinal Disorder

The terms "chronic gastrointestinal disorder," "gastrointestinal epithelial cell barrier function disorder," "chronic disease related to disruption of the intestinal epithelial barrier," and the like refer to conditions in which individuals have chronic or recurring immune response and inflammation of the gastrointestinal (GI) tract. The most common diseases or disorders are irritable bowel syndrome (IBS), inflammatory bowel disease (IBD), Crohn's disease (CD), ulcerative colitis (UC), and celiac disease. Other chronic gastrointestinal disorders include, but are not limited to, necrotizing enterocolitis, indeterminate colitis, chronic colitis, HIV enteropathy, *Helicobacter* gastritis, NSAID-enteropathy/enteritis, pouchitis, discontinuous or patchy disease, ileal inflammation, extracolonic inflammation, granulomatous inflammation in response to ruptured crypts, aphthous ulcers, transmural inflammation, microscopic colitis, diverticulitis, diversion colitis, short bowel syndrome, GI mucositis, chemotherapy induced mucositis, radiation induced mucositis, and interstitial cystitis.

Ulcerative colitis (UC). UC is a disease that causes inflammation and sores, called ulcers, in the lining of the large intestine. The inflammation usually occurs in the rectum and lower part of the colon, but it may affect the entire colon. UC may occur in people of any age and is believed to be the result of the body's immune system reacting to a virus or a bacterium by causing ongoing inflammation in the intestinal wall. People with ulcerative colitis have abnormalities of the immune system, but it has not been shown that these abnormalities are the cause or the result of the disease.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps.

Crohn's Disease (CD). Crohn's disease is characterized by intestinal inflammation and the development of intestinal stenosis and fistulas; neuropathy often accompanies these symptoms. In some instances, it is believed that Crohn's disease results from a failure of the intestinal mucosal barrier, possibly resulting from genetic susceptibilities and environmental factors (e.g., smoking), which exposes the immune system to antigens from the intestinal lumen including bacterial and food antigens. Another hypothesis is that persistent intestinal infection by pathogens such as *Mycobacterium paratuberculosis*, *Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce.

The presence of IgA and IgG anti-*Saccharomyces cerevisiae* antibodies (ASCA) in the serum has been found to be highly diagnostic of pediatric Crohn's disease. Further, in active cases of Crohn's disease, elevated concentrations of TNF-α and IL-6 are secreted into the blood circulation, and TNF-α, IL-I, IL-6, and IL-8 are produced in excess locally by mucosal cells. In this respect, it has been suggested that cytokine profiles in stool samples could be a useful diagnostic tool for Crohn's disease.

Irritable Bowel Syndrome (IBS). IBS is a disorder that affects mainly the bowel or large intestine. IBS causes cramping, bloating, gas, diarrhea, and constipation. With IBS, the nerves and muscles in the bowel are extra sensitive and may be activated during or shortly after a meal or exercise thereby cramping and diarrhea. Foods that tend to cause symptoms include milk products, chocolate, alcohol, caffeine, carbonated drinks, and fatty foods. In some cases, simply eating a large meal will trigger symptoms.

Necrotizing Enterocolitis. Necrotizing enterocolitis is an acquired disease, primarily in premature infants or sick newborns, in which intestinal tissue dies. In necrotizing enterocolitis, the lining of the intestinal wall dies and the tissue sloughs off. The cause for this disorder is unknown, but it is thought that a decreased blood flow to the bowel keeps the bowel from producing the normal protective mucus. Bacteria in the intestine may also be a cause. At risk are small, premature infants, infants who are fed concentrated formulas, infants in a nursery where an outbreak has occurred (suggesting an infectious cause), and infants who have received blood exchange transfusions.

Symptoms include abdominal distention, vomiting, lethargy, feeding intolerance, blood in the stool, temperature instability, and diarrhea. Diagnosis usually involves abdominal x-ray, and examination for occult stool blood, elevated white count, thrombocytopenia, and lactic acidosis.

Celiac Disease. Celiac disease is a digestive disease that damages the small intestine with absorption of nutrients from food. People who have digestive interferes who have celiac disease cannot tolerate gluten, a protein found in wheat, rye, and barley. When people with celiac disease eat foods or use products containing gluten, their immune system responds by damaging the small intestine.

Celiac disease is a genetic disease, which may be triggered or become active for the first time after surgery, pregnancy, childbirth, viral infection, or severe emotional stress. A subject with celiac disease may present with diarrhea and abdominal pain, irritability, depression, gas, recurring abdominal bloating, foul-smelling or fatty stool, weight loss/gain, fatigue, unexplained anemia, bone or joint pain, osteoporosis, osteopenia, behavioral changes, tingling numbness in the legs (from nerve damage), muscle cramps, seizures, missed menstrual periods (often because of excessive weight loss), infertility, recurrent miscarriage, delayed growth, failure to thrive in infants, pale sores inside the mouth (called aphthous ulcers), tooth discoloration or loss of enamel, and itchy skin rash (dermatitis herpetiformis). Celiac disease may be diagnosed using a test blood for measuring levels of Immunoglobulin A (IgA), anti-tissue transglutaminase (tTGA) and IgA antiendomysium antibodies (AEA).

HIV Enteropathy. HIV enteropathy is a syndrome characterized by chronic, well-established diarrhea (greater than one month in duration) without an identified infectious cause after thorough evaluation, in an HIV-positive individual. It is thought to be due to direct or indirect effects of HIV on the enteric mucosa.

Helicobacter Gastritis. *Heliobacter pylori* can cause infections of the stomach that may contribute to the development of dyspepsia (heartburn, bloating and nausea), gastritis (inflammation of the stomach), and ulcers in the stomach and duodenum. *H. pylori* infection can be diagnosed by endoscopic biopsy followed by testing of the removed tissue for the bacteria, a breath test, or a blood test (measuring antibodies against these bacteria present in the blood). Symptoms include discomfort, bloating, nausea and perhaps vomiting, as well as ulcers.

NSAID-Enteropathy/Enteritis. The anti-inflammatory, analgesic, and anti-pyretic properties of NSAIDs are well established and can be used in a wide range of disorders. A major limitation of NSAIDs' clinical utility is their gastroduodenal epithelial toxicity. NSAID toxicity is not site-specific to the gastroduodenum, and can induce toxicity in the more distal intestine.

Digestive Health

This disclosure provides methods for improving, restoring, or maintaining digestive health. In accordance with such methods, an effective amount of a compound or extract of this disclosure is provided to a subject in need thereof so that the subject's digestive function is improved or maintained thereby addressing the underlying pathogenesis of one or more chronic gastrointestinal disorders and promoting the health, well-being, and quality of life of the subject. The term "subject" as used herein refers to an animal, preferably a mammal. In some embodiments, the subject is a veterinary, companion, farm, laboratory or zoological animal. In other embodiments, the subject is a human.

In some aspects, a composition comprising a compound of Formula (I), Formula (II), or Formula (III), or a pharmaceutically acceptable salt thereof, isomer, homodimer, heterodimer, or conjugate, improves digestive health in a subject. In some embodiments, a composition comprising a compound of Formula (I), Formula (II), or Formula (III) treats or ameliorates a disease or condition associated with digestive health in a subject. In some embodiments, treating or ameliorating digestive health in a subject is not treatment or improving of inflammation. In some embodiments, a composition comprising a compound of Formula (I), Formula (II), or Formula (III) treats or ameliorates a disease or condition associated with digestive health in a subject by increasing HNF4α expression. In some embodiments, a composition comprising a compound of Formula (I), Formula (II), or Formula (III) treats or ameliorates a disease or condition associated with digestive health in a subject reverses the loss of Paneth cells that occur from a high fat diet. In some embodiments, a composition comprising a compound of Formula (I), Formula (II), or Formula (III) treats or ameliorates a disease or condition associated with digestive health in a subject increases intestinal villus. In some embodiments, a composition comprising a compound of Formula (I), Formula (II), or Formula (III) treats or ameliorates a disease or condition associated with digestive health in a subject by increasing Paneth cell formation. In some embodiments, a composition comprising a compound of Formula (I), Formula (II), or Formula (III) treats or ameliorates a disease or condition associated with digestive health in a subject by decreasing a condition associated with an allergic response.

In an embodiment, a composition comprising a compound of Formula (I), Formula (II), or Formula (III), or a pharmaceutically acceptable salt thereof, treats or improves at least one factor associated with digestive health of a subject. In other aspects, a composition comprising a compound of Formula (I), Formula (II), or Formula (III), or a pharmaceutically acceptable salt thereof disclosed herein improves digestive health of a subject by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects, a composition comprising Formula (I), Formula (II), or Formula (III), or a pharmaceutically acceptable salt thereof, improves digestive health by of reducing a disease or condition associated with digestive health from a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%. In some embodiments, disease or condition associated with digestive health level of Paneth cells, HNF4α level, allergic response, or intestinal villus levels In an embodiment, a composition comprising a compound of Formula (I), Formula (II), or Formula (III), or a pharmaceutically acceptable salt thereof, has an anti-inflammatory activity capable of reducing the levels of an inflammation in the liver or intestine. In other aspects, a composition comprising a compound of Formula (I), Formula (II), or Formula (III), or a pharmaceutically acceptable salt thereof disclosed herein has an anti-inflammatory activity capable of reducing the levels of a inflammation by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects, a composition comprising Formula (I), Formula (II), or Formula (III), or a pharmaceutically acceptable salt thereof, has an anti-inflammatory activity capable of reducing the levels of an inflammation in the liver or intestines from a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%. In some embodiments, the inflammation is chronic inflammation. In some embodiments, the composition reduces a symptom associated with inflammation. In some embodiments, the composition treats, reduces, or eliminates a symptom associated with inflammation in a subject. In some embodiments, the composition treats, reduces, or eliminates inflammation in a subject.

In some embodiments, inflammation symptoms may include, without limitation, edema, hyperemia, erythema, bruising, tenderness, stiffness, swollenness, fever, chills, stuffy nose, stuffy head, breathing problems, fluid retention, blood clots, loss of appetite, increased heart rate, formation of granulomas, fibrinous, pus, non-viscous serous fluid, or ulcer and pain.

In some embodiments, inflammation symptoms can be associated with a large, unrelated group of disorders which underlay a variety of diseases and disorders. In some embodiments, the immune system is often involved with inflammation disorders, demonstrated in both allergic reactions and some myopathies, with many immune system disorders resulting in abnormal inflammation.

A subject in need of a composition of this disclosure includes a subject with observable symptoms of a chronic gastrointestinal disorder (e.g., a subject with abdominal pain, blood in stool, pus in stool, fever, weight loss, frequent diarrhea, fatigue, reduced appetite, tenesmus, and rectal bleeding), as well as a subject who has no observable symptoms of a chronic gastrointestinal disorder but has been determined to be susceptible to developing the gastrointestinal disorder (i.e., a subject at risk of developing the gastrointestinal disorder)

The term "effective amount" as used herein means an amount of the compound, extract, or formulation containing the compound or extract, which is sufficient to significantly improve a disorder. As used herein, the term "improve" or "improved" should be taken broadly to encompass improvement in an identified characteristic of a disease state, said characteristic being regarded by one of skill in the art to generally correlate, or be indicative of, the disease in question, as compared to a control, or as compared to a known average quantity associated with the characteristic in question. For example, "improved" digestive health associated with application of a compound or extract of the disclosure can be demonstrated by comparing the digestive health (e.g., abdominal symptoms, stool, fever, weight, appetite and/or epithelial barrier integrity) of a human treated with the compound or extract, as compared to the digestive health of a human not treated. Alternatively, one could compare the digestive health of a human treated with a compound or extract of the disclosure to the average digestive health of a human, as represented in scientific or medical publications known to those of skill in the art. In the present disclosure, "improved" does not necessarily demand that the data be statistically significant (i.e., p<0.05); rather, any quantifiable difference demonstrating that one value (e.g., the average treatment value) is different from another (e.g., the average control value) can rise to the level of "improved."

Of concern when determining an effective amount to be used in humans is balancing the desired effects (benefits) against risks associated with use of a compound. At issue for such risk/benefit assessments is the types of adverse effects observed and the likelihood that they will occur. Also considered is the fact that the effective amount may vary with the particular disorder being treated, e.g., IBD, IBS, UC, or CD, the age and physical condition of the end user, the severity of the condition, the duration of the treatment, the particular carrier utilized, and like factors.

In general, a suitable daily dose of a compound or extract of the disclosure will be that amount of a compound or extract which is the lowest dose that is effective at producing a desired benefit, in this case an effect that improves digestive health and consequently overall health and well-being. Such an effective dose will generally depend upon the factors described herein. For oral administration, the dose may range from about 0.0001 mg to about 10 grams per kilogram of body weight per day, about 5 mg to about 5 grams per kilogram of body weight per day, about 10 to about 2 grams per kilogram of body weight per day, or any other suitable dose. If desired, the effective daily dose of the compound or extract may be administered as two, three, four, five, six or more sub-doses administered separately at appropriate intervals throughout the day, optionally, in unit dosage forms. In some embodiments, dosing is one administration per day.

The compound or extract of the disclosure can be used alone or in combination with a particular diet or standard of care. By way of illustration, a compound or extract of this disclosure may be combined with a gluten-free diet, or used in combination with an aminosalicylate, a corticosteroid, athiopurine, methotrexate, a JAK inhibitor, a sphingosine 1-phosphate (SIP) receptor inhibitor, an anti-integrin biologic, an anti-IL12/23R or anti-IL23 biologic, and/or an anti-tumor necrosis factor agent or biologic.

Administration of a compound or extract of the disclosure improves digestive function thereby addressing the underlying pathogenesis of one or more gastrointestinal disorders and promoting the health, well-being, and quality of life of the subject. Ideally, an effective amount of a compound or extract provides a measurable improvement in the levels or activity of HNF4α activity and/or intestinal epithelial barrier and/or digestive function compared to a subject not receiving treatment. More particularly, use of a compound or extract of the disclosure preferably prevents, slows the progression of, delays or treats an intestinal disorder such as IBD, IBS, UC and/or CD.

The following non-limiting examples are provided to further illustrate the present disclosure.

Example 1: Assessing Indicators of Metabolic Activity: Materials and Methods

Expression of Insulin and HNF4α. RNA was purified using a RNEASY® chromatographic separation and isolation kits (Qiagen), and converted to cDNA using the gScript™ cDNA SuperMix (Quanta Biosciences). Q-PCR was conducted with cDNA corresponding to 2 μg of RNA using an Optic on Real-Time System (MJ Research) and QPCR SuperMix (BioPioneer). See All mRNA values were normalized to 18S rRNA values and are expressed as fold changes over vehicle-treated control.

Primary Antibodies. HNF4α antibodies were used (#sc-6556, Santa Cruz Biotechnology; Santa Cruz, Calif. and #3113, Cell Signaling Technology; Danvers, Mass.). For fluorescent imaging, samples were incubated with ALEXA FLUOR® 488 green-fluorescent dye or Rhodamine labeled anti-mouse, rabbit or goat and nuclei were counterstained with DAPI (4',6-diamidino-2-phenylindole). antibodies alone were used immunostaining. Fluorescently Controls to ensure labeled using secondary specificity of sections were analyzed with a conventional inverted microscope (Olympus, PlanFl 40×/0.60) or with a confocal microscope equipped with a krypton/argon laser.

Bioavailability Determinations. Male C57BL/6 mice were administered N-trans-caffeoyl tyramine or N-transferuloyl tyramine via IV, intraperitoneal or oral route (three mice for each route) (Table 2).

TABLE 2

| Route | Formulation | Dosage (mg/kg) |
| --- | --- | --- |
| IV | 1 mg/mL in 75% PEG 300/25% water, clear solution | 2.0 |
| Oral | 3 mg/mL in 0.5% methyl cellulose, homogenous opaque suspension with fine particles | 30.0 |
| IP | 3 mg/mL in 5% DMSO/5% Polysorbate 80/90% water, clear solution | 30 |

A blood sample from each mouse was drawn at 0.25, 0.5, 1, 2, 4, 6 and 24 hours after administration. An 8 μL aliquot of blood was used for analysis. After adding 200 μL of an internal standard comprising 100 ng/mL Labetalol, 100 ng/mL dexamethasone, 100 ng/mL tolbutamide, 100 ng/mL Verapamil, 100 ng/mL Glyburide, and 100 ng/mL Celecoxib in ACN, the mixture was vortex-mixed and centrifuged at 12000 rpm for 15 minutes at 4° C. to pellet precipitated protein. Four μL of the supernatant was injected for LC-MS/MS analysis. Bioavailability (%) was calculated using $AUC_{0-inf}$ (% $AUC_{Extra}$<20%) or $AUC_{0-last}$(% $AUC_{Extra}$>20%) with nominal dose.

pH Stability Assessment. Individual stock solutions were prepared in DMSO at concentrations of 10 mg/mL. Four different buffer solutions were prepared to achieve solutions with a pH of 2, 7.4, 8.5 and 10. For each pH assay, 5 μL of stock solution was added to 245 μL of buffered solution to a 2 mL tube, vortexed and incubated in a 37° C. water bath. At each timepoint, 50 μL aliquots were taken, neutralized and analyzed via HPLC analysis using a DAD detector at 280 nm. The fold change of the peak area at 280 nm was analyzed for the initial and final timepoint, 0.5 and 72 hours, respectively.

Example 2: Assessing Compounds for Activity as HNF4α Agonists

Given the role of HNF4α in maintaining a healthy metabolism in humans, test compounds were screened for activity as HNF4α agonists (either direct or indirect effects). Using a known insulin promoter-reporter assay, Kiselyuk and colleagues (2010. *J. Biomol. Screen* 15(6): 663-70), screened a library of compounds for activity to promote insulin activation. They identified compound 1 as an insulin activator (Kiselyuk, et al. (2012) *Chem. Biol.* 19(7): 806-18) and the compound was subsequently shown to possess HNF4α agonistic activity in an ornithine transcarbamoylase (OTC) promoter assay. The OTC promoter is known to be responsive to HNF4α in transient transfection assays (Inoue, et al. (2002) *J. Biol. Chem.* 277:25257-65).

To identify plant compounds that have similar bioactivity as this synthetic agent (compound 1), a bioinformatics approach was taken to predict, from the set of all known plant compounds, a targeted sub-set with the desired HNF4α agonistic activity. Using a number of algorithms in combination with training data (i.e., positive data), models were built around important features of the positive data, which were predictive of the desired biological activity. More specifically, a set of 18 synthetic compounds with known ability to affect HNF4α activity (e.g., compound 1) were included in the positive data set. These structures were used to search a database of plant compounds for chemical structures that had similar structural features. A number of metrics were used to measure similarity based on concepts from the fields of graph theory and information theory, either solely or in combination.

Plant compounds in the top 10th percentile of similarity to the 18 target structures were selected and compounds predicted to be potential agonists of HNF4α activity given their chemical structural features were screened in the HNF4α assay. The results of the screening identified a class of plant tyramine containing hydroxycinnamic acid amides (i.e., N-transcaffeoyltyramine, N-cis-caffeoyltyramine, N-trans-feruloyltyramine and p-coumaroyltyramine) that are able to act as HNF4α modulators. Notably, N-trans-caffeoyltyramine was determined to be roughly an order-of-magnitude more potent than Alverine in activating HNF4α (FIG. 1). Due to hydroxyl derivatization of both phenyl rings, N-transcaffeoyltyramine is less lipophilic and therefore expected to be more bioavailable. Overall, the increased potency and expected enhanced bioavailability indicated that N-transcaffeotyramine and other tyramine containing hydroxycinnamic acid amides would be expected to be more desirable compounds for use in the methods disclosed herein.

Figure 2:
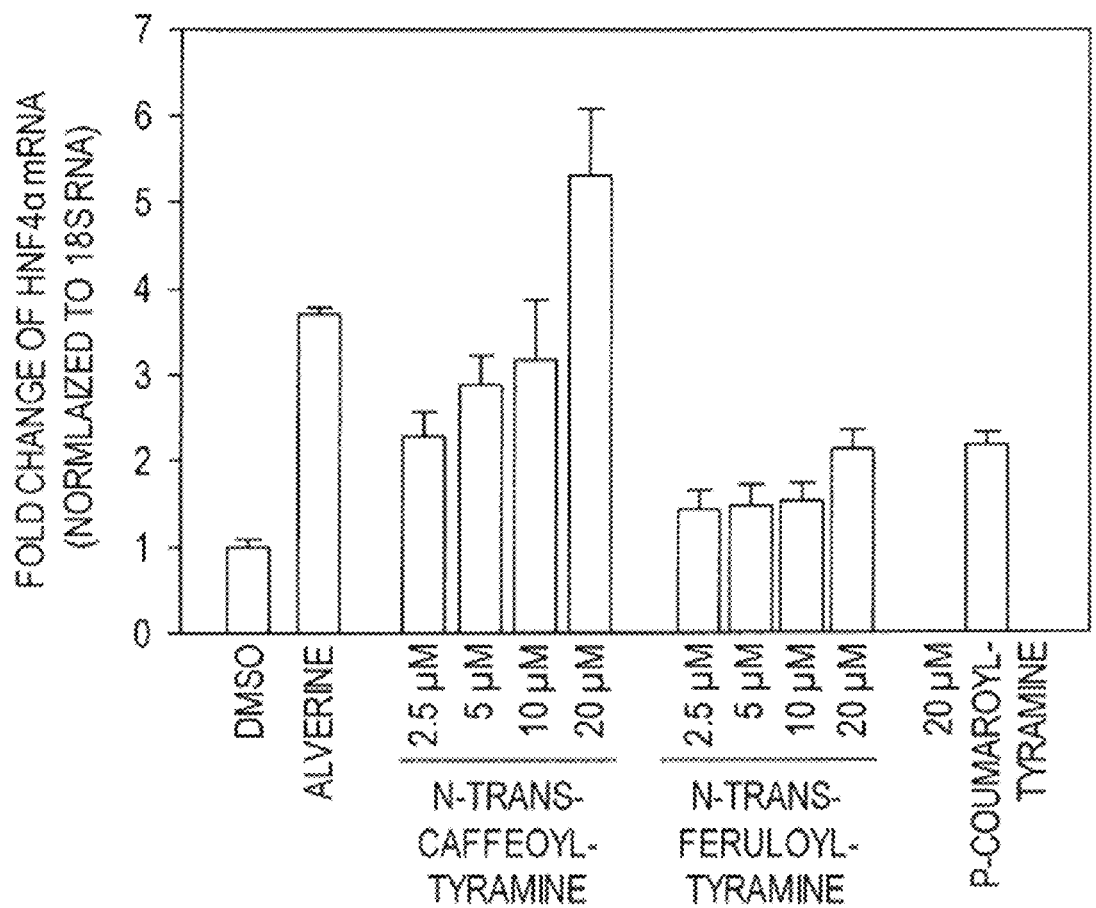
FIG. 2 illustrates the effect of N-trans-caffeoyltyramine, N-trans-feruloyltyramine and p-coumaroyltyramine on HNF4α mRNA levels as determined by quantitative PCR. DMSO and alverine (20 μM) were used as negative and positive controls, respectively.

Experiments were performed to demonstrate that these compounds directly modulate HNF4α activity. In particular, it was demonstrated that HNF4α gene expression was upregulated (e.g., as determined by quantitative PCR analysis) in the presence of N-trans-caffeoyl tyramine and N-trans-feruloyltyramine (FIG. 2). In addition, it was found that p-coumaroyltyramine also upregulated HNF4α gene expression; however, cis-feruloyltyramine, N-coumaroyldopamine, N-trans-feruloyloctopamine and pcoumaroyloctopamine were inactive.

Example 3: Evaluation of Compound-Related Toxicity

Given the need to balance benefits and risks of the compounds of the present disclosure, in vivo toxicity studies in laboratory animals (e.g., mice, rats, dogs) are typically performed. Such studies are typically performed consistent with Good Laboratory Practice (GLP) regulations to ensure reliability and reproducibility for regulatory purposes. If compounds are to be administered for periods of weeks to months to years in humans, chronic toxicity studies typically are performed (studies of from six months to one year in duration). For compounds to be used in foods, oral toxicity studies are recommended.

The purpose of chronic toxicity testing is to determine the toxicological profile of a test compound. In the initial phase of testing, a study will be performed in rats. A total of 160 Sprague Dawley rats (80 males and 80 females) approximately 5-7 weeks old and weighing between 80-100 g each will be randomly selected and allocated to treatment groups by weight; such that the mean body weights of each group will not be significantly different. The test compound or extract will be administered orally at dose levels of 0.5, 1 and 2 g/kg body weight per day to rats for a period of 90 consecutive days. The animals will be observed daily for any clinical signs of toxicity (e.g., behavioral changes; skin and fur appearance; eating and drinking; etc.). At the end of the experiment, the animals will be subjected to hematological, biochemical and histopathological evaluation consistent with standard toxicological methods.

Initial safety/toxicity assays were also performed, the collective results of which are presented in Table 3.

TABLE 3

| Assay | N-trans-caffeoyl tyramine | N-trans-feruloyl tyramine | p-coumaroyl tyramine |
|---|---|---|---|
| HNFα Activity | + | + | + |
| HNFα mRNA | + | + | + |
| Insulin mRNA | + | + | + |
| Estrogenic Counter-Screen | + | + | + |
| pH Stability | Acid Stable | Stable | Acid Stable |
| Bioavailability | ~11% | ~7% | ND |

ND, not determined.

Example 4: Isolation of Tyramine Containing Hydroxycinnamic Acid Amides from Plant Sources Ethanolic extracts were prepared from various plant species and plant tissues thereof. Individual compounds were identified in the extracts by extracting dry plant powder material with 95% aqueous ethanol. The ethanol extract was concentrated and adsorbed onto celite and dryloaded onto a C18 solid phase extraction column. The extract was desalted by washing with two column volumes of water which were collected and discarded. Compounds were eluted with two column volumes of methanol and the extract was concentrated to dryness. The extract was resuspended in 1:1 Acetonitrile:water prior to analysis. Synthetic standards of known concentrations were used to generate calibration curves prior to analysis. The listing of sources used in the analysis are presented below in Table 4. Plants are displayed for each compound in descending order with the plants that produce the highest amount of compound on the top of the list and the lowest producers at the bottom of the list.

TABLE 4

| Genus species | Plant Tissues(s) |
|---|---|
| N-Trans-caffeoyltyramine | |
| Annona muricata | Seed, pulp, skin |
| Annona spp. | Seed, pulp, skin |
| Tribulus terrestris | Seed, fruit |
| Cannabis sp. | Seed, hull, leaf |
| Annona cherimola | Seed, pulp, skin, leaf, wood |
| Annona montana | Leaf |
| Solanum lycopersicum | Fruit |
| Solanum tuberosum | Tuber, peel |
| Lycium barbarum | Fruit, stem |
| N-Trans-feruloyltyramine | |
| Annona spp. | Seed, pulp, skin |
| Annona cherimola | Seed, pulp, skin, leaf, wood |
| Piper nigrum | Fruit |
| Tribulus terrestris | Seed, fruit |
| Annona muricata | Seed, pulp, skin |
| Solanum lycopersicum | Fruit |
| Cannabis | Seed, hull, leaf |

TABLE 4-continued

| Genus species | Plant Tissues(s) |
|---|---|
| Capsicum frutescens | Fruit |
| Allium fistulosum | Aerial plant |
| Solanum tuberosum | Tuber, peel |
| Zea mays | Seed, stalk, leaf |
| Allium sativum | Bulb |
| Annona montana | Leaf |
| Annona squamosa | Fruit |
| Lycium barbarum | Fruit, stem |
| Capsicum annuum | Fruit |
| Ipomoea batatas | Peel |
| Chenopodium quinoa | Seed |
| Annoracia rusticana | Root |
| Capsicum annuum | Fruit, leaf, stem |
| Fagopyrum esculentum | Hull |
| Eragrostis tef | Seed |
| p-Coumaroyltyramine | |
| Annona spp. | Seed, pulp, skin |
| Tribulus terrestris | Seed, fruit |
| Solanum lycopersicum | Fruit |
| Annona muricata | Seed, pulp, skin |
| Annona montana | Leaf |
| Annona cherimola | Seed, pulp, skin, leaf, wood |
| Cannabis spp. | Seed, hull, leaf |
| Solanum tuberosum | Tuber, peel |
| Allium fistulosum | Aerial plant |
| Zea mays | Seed, stalk, leaf |
| Allium sativum | Bulb |
| Ipomoea batatas | Peel |

Figure 3:
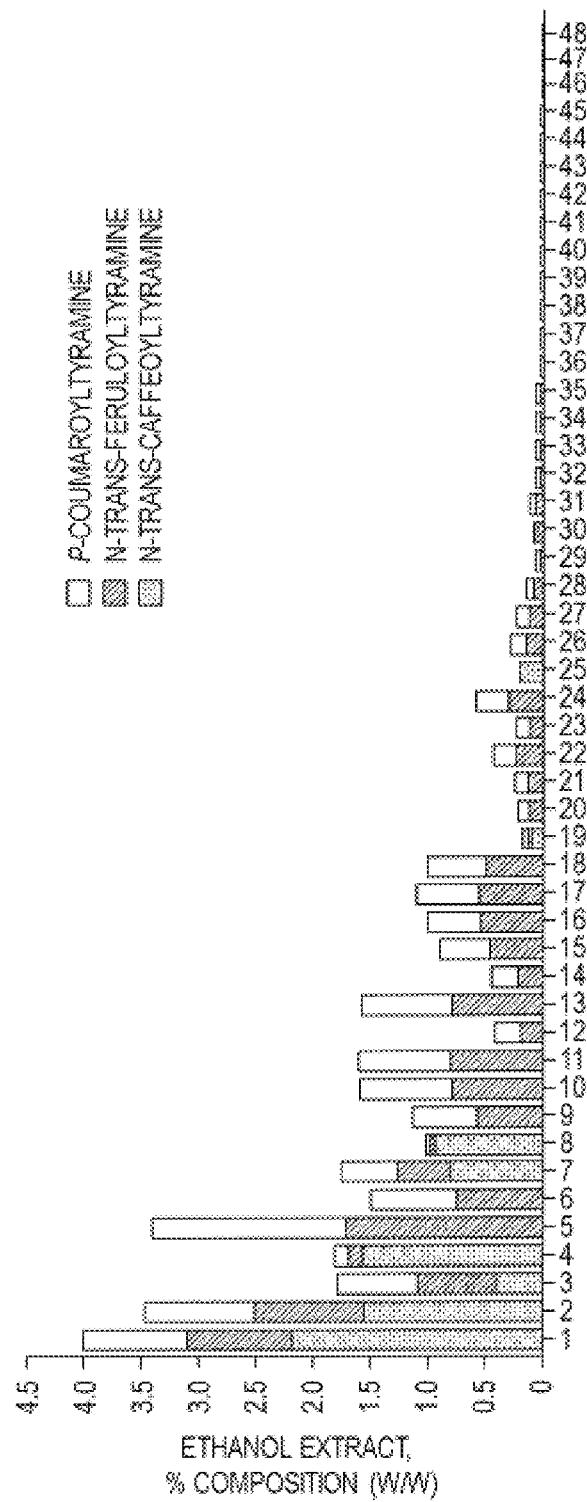
FIG. 3 illustrates the amounts of N-trans-caffeoyltyramine, N-trans-feruloyltyramine and p-coumaroyl tyramine present in ethanol extracts (% of extract, w/w) from a variety of sources including *Tribulus terrestris* seed (1), *Cannabis* (hemp) seed hull (2), *Annona* spp. (atemoya) seed (3), *Annona muricata* (Guanabana) seed (4), *A. cherimola* (Cherimoya) leaf (5), *Zea mays* stalk (6), *Tribulus terrestris* (Goat Head) seed (7), *A. cherimola* hardwood (bark and core) (8), *Solanum lycopersicum* ground pomace (9), *S. tuberosum* (yellow potato) peel (10), *Piper nigrum* (black peppercorn) fruit (11), *S. tuberosum* (purple potato) peel (12), *S. tuberosum* (red potato) peel (13), *S. lycopersicum* pomace (14), *S. lycopersicum* extruded pomace (15), *A. muricata* (Guanabana) leaves (16), *Allium sativum* (garlic) bulb (17), *S. tuberosum* (purple potato) peel (18), *A. montana* (Mountain soursop) leaves (19), *Z. mays* leaves (20), *S. tuberosum* (purple potato) sprouts (21), *A. cherimola* (Cherimoya) seed (22), *Allium fistulosum* (green onion) whole plant (23), *S. tuberosum* (white potato) peel (24), *A. cherimola* (Cherimoya) greenwood (25), *Cannabis* (hemp) leaves (26), *S. tuberosum* (white potato) peel (27), *S. lycopersicum* seed (28), *S. lycopersicum* (Beefsteak) whole fruit (29), *A. muricata* (Guarabana) skin of unripe fruit (30), *A. muricata* (Guanabana) ripe fresh fruit (31), *A. squamosa* (sweetsop) whole fruit (32), *Capsicum annuum* (serrano pepper) fruit (33), *S. tuberosum* (Russet potato) peel (34), *Lycium barbarum* (goji/wolf berry) fruit (35), *S. tuberosum* (purple potato) core (36), *Chenopodium quinoa* (quinoa) seed (37), *Ipomoea batatas* (sweet potato) whole potato (38), *Ipomoea batatas* (sweet potato) peel (39), *Armoracia rusticana* (horseradish) root (40), *S. tuberosum* (Colorado potato) peel (41), *Fagopyrum esculentum* (buckwheat) hulls (42), *Capsicum frutescens* (piri piri pepper) fruit (43), *S. tuberosum* (purple potato) core (44), *C. annuum* (Thai chili) stems and leaves (45), *A. muricata* (Guanabana) unripe fruit flesh (46), *S. tuberosum* (yellow potato) core (47), and *Eragrostis tef* (teff) seed (48).

The amounts of N-trans-caffeoyltyramine, N-transferuloyltyramine and p-coumaroyltyramine present in certain ethanol extracts (% of extract, w/w) was determined. Quantification of the compounds was performed by normalizing the results by the weight of the ethanol extracts (FIG. 3).

Example 5: N-Trans-Caffeoyltyramine Improves Tight Junctions

TNF-α is an inflammatory cytokine that increases intestinal tight junction permeability. To analyze the effect of N-trans-caffeoyltyramine on tight junctions, 200 ng or 300 ng TNF-α was added to a monolayer of epithelial CaCo-2 cells to induced tight junction damage. After TNF-α exposure, N-trans-caffeoyltyramine was added and tight junction formation was determined by antibody staining for zonula occludens (ZO) –1. Nuclear stain (DAPI) was used to demonstrate cell viability. The CaCo-2 cells was sorted for high TNF-α expression with compromised integrity of tight junctions. Increasing concentration of exogenous TNF-α from 200 ng to 300 ng reduced ZO-1 staining. However, N-transcaffeoyltyramine addition reversed the effects of TNF-α on ZO-1 at both the 200 ng to 300 ng amounts.

To confirm the in vivo caffeoyltyramine, C57BL/6 mice effect intraperitoneal injection (IP) caffeoyltyramine twice a day for 14 were with days. of N-transdosed by N-transIntestinal samples were harvested and stained to visualize HNFα expression, ZO-1 and DAPI staining. HNF4α expression was observed in the stem cells of the epithelial layer in all mice. Extension of HNF4α expression along the villi of the epithelial was visible after 2 weeks of treatment with N-trans-caffeoyl tyramine demonstrating that this compound induced HNF4α expression in the intestinal lining of N-trans-caffeoyltyramine-treated mice.

Example 6: Effect of N-Trans-Caffeoyltyramine on the Intestine

Figure 4:
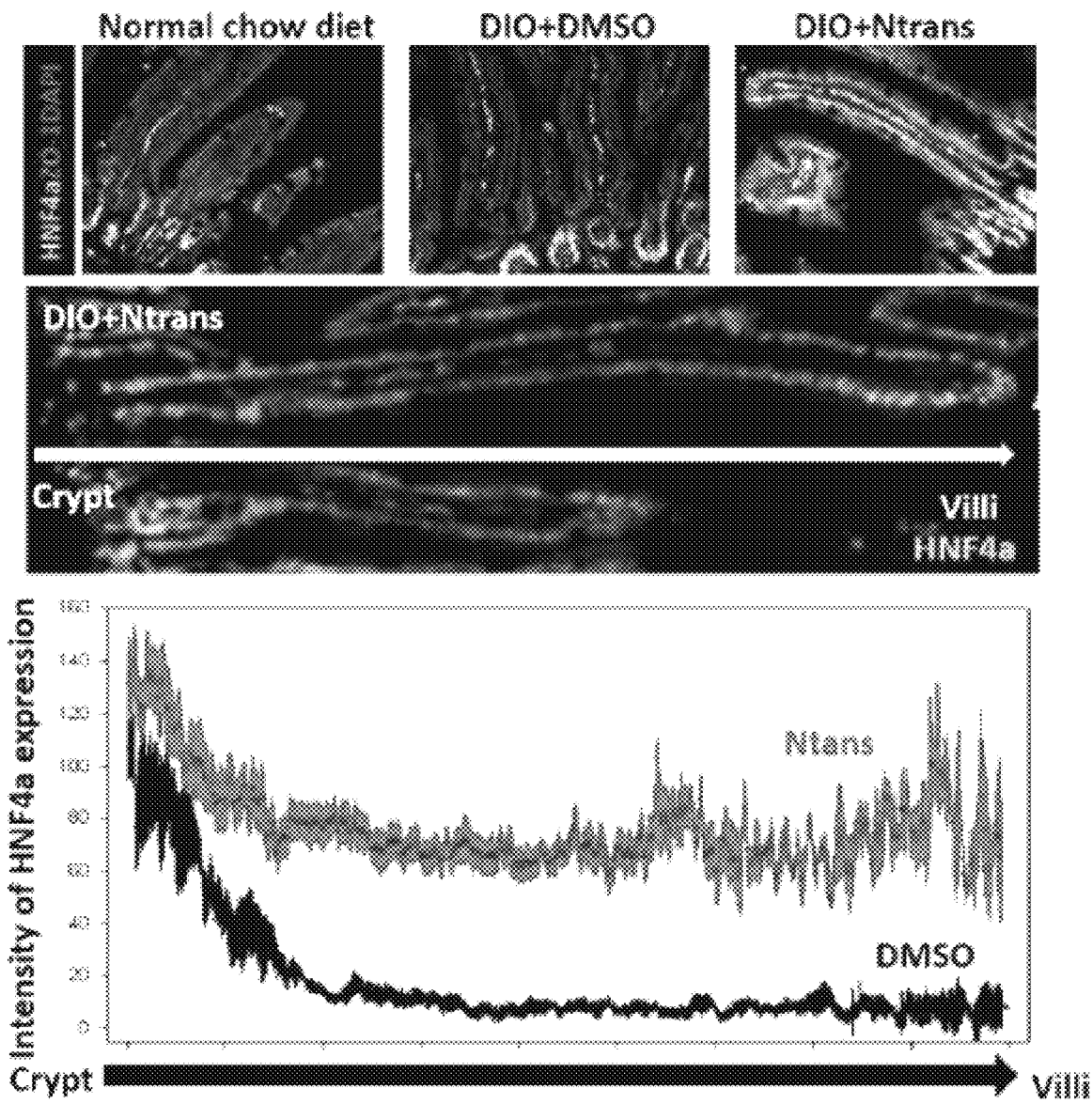
FIG. 4 illustrates HNF4α is increased in the intestine of DIO mice treated with NCT.
Figure 5:
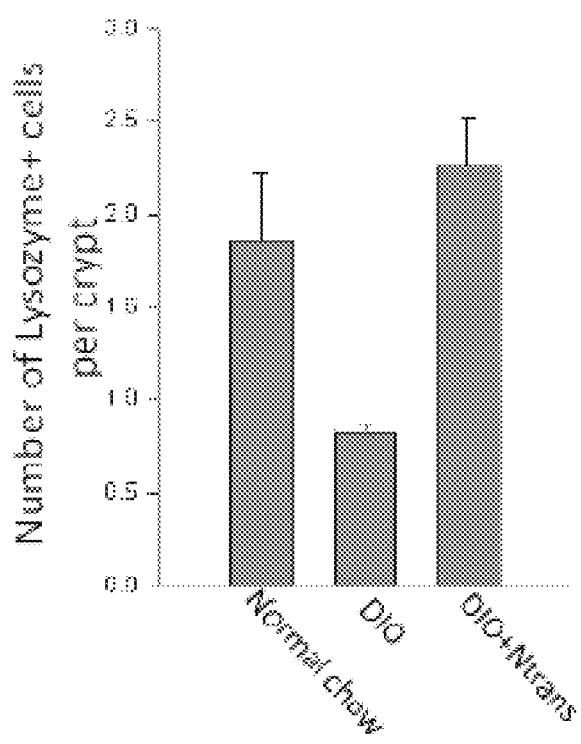
FIG. 5 illustrates paneth cells are increased in the intestine of DIO mice treated with NCT.

Intestine from mice treated with DMSO or N-trans-caffeoyltyramine were examined histologically. Gross morphological appearance was unchanged. DIO mice did not exhibit significant change in HNF4α expression. In both, HNF4α was highly expressed in the crypt, with much less being detectable in the villi (see FIG. 4). N-trans-caffeoyltyramine induced a large increase in HNF4α expression throughout, with a large increase in the villi and a smaller increase in the crypt, where expression was already quite strong (see FIG. 5, quantified in lower panel). Analysis of genes induced by N-trans-caffeoyltyramine suggested that N-trans-caffeoyltyramine may be promoting Paneth cell formation and/or function. Paneth cells are specialized secretory cells that play a critical role in defenses against intestinal microbes. To that end, they secrete a variety of antimicrobial peptides. Of note, Paneth cells play an important role in IBD pathogenesis. High fat diet has been reported to reduce the number of Paneth cells, and our studies reproduced that finding (see FIG. 4), but the mechanism by which that occurs has not been understood. Remarkably, N-trans-caffeoyltyramine induced a complete recovery in the number of Paneth cells in DIO mice (see FIG. 4).

The disclosure is generally described herein using affirmative language to describe the numerous embodiments. The disclosure also includes embodiments in which subject matter is excluded, in full or in part, such as substances or materials, method steps and conditions, protocols, or procedures. Various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating a disease or disorder selected from the group consisting of an inflammatory bowel disease, irritable bowel syndrome, ulcerative colitis, celiac disease, and Crohn's disease in a human in need thereof comprising orally administering to the human in need thereof a therapeutically effective amount of a pharmaceutically acceptable carrier and an extract comprising a compound of Formula (I), or an isomer, salt, homodimer, heterodimer, or conjugate thereof:

Formula (I)

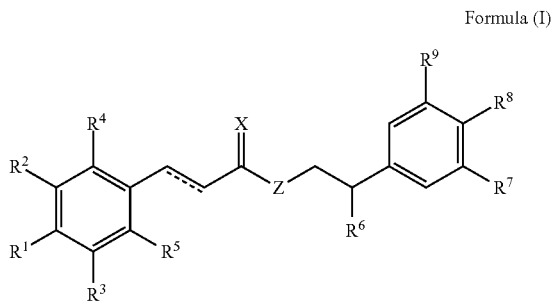

wherein $R^1$, $R^2$, $R^3$, $R^4$, $R^5$, $R^6$, $R^7$, $R^8$, and $R^9$ are each independently selected from hydrogen, deuterium, hydroxyl, halogen, cyano, nitro, amino, C-amido, N-amido, ester, —(O)$C_{1-6}$alkyl, —(O)$C_{1-6}$alkenyl, —(O)$C_{1-6}$alkynl, —(O)$C_{4-12}$cycloalkyl, —(O)$C_{1-6}$alkyl$C_{4-12}$cycloalkyl, —(O)$C_{4-12}$heterocyclyl, —(O)$C_{1-6}$alkyl$C_{4-12}$heterocyclyl, —(O)$C_{4-12}$aryl, —(O)$C_{1-6}$alkyl$C_{5-12}$aryl, —(O)$C_{1-12}$heteroaryl, and —(O)$C_{1-6}$alkyl$C_{1-12}$heteroaryl;

the dashed bond is present or absent;

X is $CH_2$ or O;

Z is $CHR^a$, $NR^a$, or O; and $R^a$ is selected from hydrogen, deuterium, hydroxyl, halogen, cyano, nitro, amino, C-amido, N-amido, ester, —(O)$C_{1-6}$alkyl, —(O)$C_{1-6}$alkenyl, —(O)$C_{1-6}$alkynl, —(O)$C_{4-12}$cycloalkyl, —(O)$C_{1-6}$alkyl$C_{4-12}$cycloalkyl, —(O)$C_{4-12}$heterocyclyl, —(O)$C_{1-6}$alkyl$C_{4-12}$heterocyclyl, —(O)$C_{4-12}$aryl, —(O)$C_{1-6}$alkyl$C_{6-12}$aryl, —(O)$C_{1-12}$heteroaryl, and —(O)$C_{1-6}$alkyl$C_{1-12}$heteroaryl;

wherein the inflammatory bowel disease, irritable bowel syndrome, ulcerative colitis, celiac disease, or Crohn's disease in the human in need thereof is effectively treated;

wherein said extract is an ethanol extract of a plant selected from the group consisting of *Allium, Amoracia, Chenopodium, Spinacia, Fagopyrum, Annona, Jatropha, Piper, Eragrostis, Zea, Nelumbo, Ipomea, Capsicum, Lycium, Solanum,* and *Tribulus*; and wherein the compound of Formula I comprises between 10% to 99% w/w of the oral composition.

2. The method of claim 1, wherein the disease or disorder is inflammatory bowel disease.

3. The method of claim 1, wherein the disease or disorder is irritable bowel syndrome.

4. The method of claim 1, wherein the disease or disorder is ulcerative colitis.

5. The method of claim 1, wherein the disease or disorder is celiac disease.

6. The method of claim 1, wherein the disease or disorder is Crohn's disease.

7. The method of claim 1, wherein R8 is hydroxyl.

8. The method of claim 1, wherein R8 is hydroxyl, the dashed bond is present, X is O, Z is $NR^a$, and $R^a$ is hydrogen.

9. The method of claim 1, wherein R3, R4, R5, R6, R7, and R9 are each hydrogen, the dashed bond is present, X is O, Z is $NR^a$, and $R^a$ is hydrogen.

10. The method of claim 1, wherein R1, R2, and R8 are each hydroxyl, R3, R4, R5, R6, R7, and R9 are each hydrogen, the dashed bond is present, X is O, Z is $NR^a$, and $R^a$ is hydrogen.

11. The method of claim 1, wherein R1 and R8 are each hydroxyl, R2 is —(O)$C_{1-6}$alkyl, R3, R4, R5, R6, R7, and R9 are each hydrogen, the dashed bond is present, X is O, Z is $NR^a$, and $R^a$ is hydrogen.

12. The method of claim 1, wherein R1 and R8 are each hydroxyl, R2, R3, R4, R5, R6, R7, and R9 are each hydrogen, the dashed bond is present, X is O, Z is $NR^a$, and $R^a$ is hydrogen.

13. The method of claim 1, wherein R8 is hydroxyl, R1, R2, R3, R4, R5, R6, R7, and R9 are each hydrogen, the dashed bond is present, X is O, Z is $NR^a$, and $R^a$ is hydrogen.

14. The method of claim 1, wherein R8 is hydroxyl, R1, R2, and R3 are each —(O)$C_{1-6}$alkyl, R4, R5, R6, R7, and R9 are each hydrogen, the dashed bond is present, X is O, Z is $NR^a$, and $R^a$ is hydrogen.

15. The method of claim 1, wherein the plant is selected from the group consisting of *Allium, Amoracia* and *Chenopodium*.

16. The method of claim 1, wherein the plant is selected from the group consisting of *Spinacia, Fagopyrum,* and *Annona*.

17. The method of claim 1, wherein the plant is selected from the group consisting of *Jatropha, Piper,* and *Eragrostis*.

18. The method of claim 1, wherein the plant is selected from the group consisting of *Zea, Nelumbo,* and *Ipomea*.

19. The method of claim 1, wherein the plant is selected from the group consisting of *Capsicum* and *Lycium*.

20. The method of claim 1, wherein the plant is selected from the group consisting of *Solanum* and *Tribulus*.

* * * * *

UNITED STATES PATENT AND TRADEMARK OFFICE
CERTIFICATE OF CORRECTION

PATENT NO. : 11,382,880 B2
APPLICATION NO. : 17/140979
DATED : July 12, 2022
INVENTOR(S) : Lee Heil Chae et al.

It is certified that error appears in the above-identified patent and that said Letters Patent is hereby corrected as shown below:

On the Title Page

Column 2 Item (56) (Other Publications), Line 2, delete "Ceils" and insert -- Cells --.

Column 2 Item (56) (Other Publications), Line 8, delete "lyramine," and insert -- tyramine, --.

Page 2, Column 1 Item (56) (Other Publications), Line 10, delete "evoution" and insert -- evolution --.

Page 2, Column 1 Item (56) (Other Publications), Line 24, delete "Saccharaomyces" and insert -- Saccharomyces --.

Page 2, Column 1 Item (56) (Other Publications), Line 34, delete "deformyiase" and insert -- deformylase --.

Page 2, Column 1 Item (56) (Other Publications), Line 35, delete "Heiicobacter" and insert -- Helicobacter --.

Page 2, Column 1 Item (56) (Other Publications), Line 52, delete "Meilitus," and insert -- Mellitus, --.

Page 2, Column 2 Item (56) (Other Publications), Line 4, delete "hypochlolesterolemic" and insert -- hypocholesterolemic --.

Page 2, Column 2 Item (56) (Other Publications), Line 6, delete "chenes" and insert -- chinense --.

Page 2, Column 2 Item (56) (Other Publications), Line 7, delete "adenysol" and insert -- adenosyl --.

Page 2, Column 2 Item (56) (Other Publications), Line 20, delete "Saccaromyces" and insert -- Saccharomyces --.

Signed and Sealed this
Sixth Day of December, 2022

Katherine Kelly Vidal
*Director of the United States Patent and Trademark Office*

Page 2, Column 2 Item (56) (Other Publications), Line 23, delete "fermentaion" and insert -- fermentation --.

Page 2, Column 2 Item (56) (Other Publications), Line 56, delete "hydroxycinnamioc" and insert -- hydroxycinnamic --.

Page 2, Column 2 Item (56) (Other Publications), Line 60, delete "ammonica," and insert -- ammonia, --.

Page 3, Column 1 Item (56) (Other Publications), Line 12, delete "curant" and insert -- currant --.

Page 3, Column 1 Item (56) (Other Publications), Line 29, delete "oftyramine" and insert -- of tyramine --.

Page 3, Column 1 Item (56) (Other Publications), Line 40, delete "phosphase" and insert -- phosphate --.

Page 3, Column 1 Item (56) (Other Publications), Line 48, delete "evealed" and insert -- revealed --.

Page 3, Column 1 Item (56) (Other Publications), Line 59, delete "ceil" and insert -- cell --.

Page 3, Column 2 Item (56) (Other Publications), Line 5, delete "Aiverine" and insert -- Alverine --.

Page 3, Column 2 Item (56) (Other Publications), Line 8, delete "stirnulated" and insert -- stimulated --.

Page 3, Column 2 Item (56) (Other Publications), Line 39, delete "Eschericia" and insert -- Escherichia --.

Page 3, Column 2 Item (56) (Other Publications), Line 40, delete "enzymative" and insert -- enzymatic --.

Page 3, Column 2 Item (56) (Other Publications), Line 49-50, delete "Saccharamyces" and insert -- Saccharomyces --.

Page 3, Column 2 Item (56) (Other Publications), Line 62, delete "dificient" and insert -- deficient --.

Page 4, Column 1 Item (56) (Other Publications), Line 12, delete "p-courarate" and insert -- p-coumarate --.

Page 4, Column 1 Item (56) (Other Publications), Line 15, delete "a-Jlucosidase" and insert -- α-glucosidase --.

Page 4, Column 1 Item (56) (Other Publications), Line 15, delete "fislulosum)," and insert -- fistulosum), --.

CERTIFICATE OF CORRECTION (continued)
U.S. Pat. No. 11,382,880 B2

Page 4, Column 1 Item (56) (Other Publications), Line 29, delete "N-hyroxycinnamoyltransferase" and insert -- N-hydroxycinnamoyltransferase --.

Page 4, Column 1 Item (56) (Other Publications), Line 42, delete "Nonpeptidio" and insert -- Nonpeptidic --.

Page 4, Column 1 Item (56) (Other Publications), Line 57, delete "biosynthsis," and insert -- biosynthesis, --.

Page 4, Column 2 Item (56) (Other Publications), Line 15-16, delete "inAlliumby" and insert -- in Allium by --.

Page 4, Column 2 Item (56) (Other Publications), Line 16, delete "multivarate" and insert -- multivariate --.

In the Specification

Column 2, Line 53, delete "$C_{1-2}$heteroaryl," and insert -- C--heteroaryl, --.

Column 3, Line 30, delete "Amoracia," and insert -- Armoracia, --.

Column 3, Line 57, delete "4yl)" and insert -- 4-yl) --.

Column 6, Line 18, delete "(Guarabana)" and insert -- (Guanabana) --.

Column 8, Line 3, delete "halogen;" and insert -- halogen. --.

Column 10, Line 9, delete "$C_{4-12}$" and insert -- $C_{1-12}$ --.

Column 12, Line 1, delete "4" and insert -- 4. --.

Column 14, Line 41, delete "dextrine" and insert -- dextrin --.

Column 19, Line 39, delete "phenyl-hexy" and insert -- phenyl-hexyl --.

Column 20, Line 31 (approx.), delete "Barssicales" and insert -- Brassicales --.

Column 20, Line 31 (approx.), delete "Barriscaceae" and insert -- Brassicaceae --.

Column 20, Line 31 (approx.), delete "Amoracia" and insert -- Armoracia --.

Column 29, Line 42 (approx.), delete "Protealese" and insert -- Proteales --.

Column 21, Line 42, delete "Butyrophillins," and insert -- Butyrophilins, --.

Column 21, Line 62, delete "eosinophylic" and insert -- eosinophilic --.

CERTIFICATE OF CORRECTION (continued)
U.S. Pat. No. 11,382,880 B2

Column 33, Line 45, delete "disorder)" and insert -- disorder). --.

Column 34, Line 37, delete "athiopurine," and insert -- a thiopurine, --.

Column 38, Line 14 (approx.), delete "Annoracia" and insert -- Armoracia --.

In the Claims

Column 41, Line 35 (approx.), In Claim 1, delete "$C_{6-12}$aryl," and insert -- $C_{5-12}$aryl, --.

Column 41, Line 42-43 (approx.), In Claim 1, delete "Amoracia," and insert -- Armoracia, --.

Column 41, Line 42-43 (approx.), In Claim 15, delete "Amoracia" and insert -- Armoracia --.